United States Patent
Nardi et al.

(10) Patent No.: US 9,802,947 B2
(45) Date of Patent: *Oct. 31, 2017

(54) 3-OXO-TETRAHYDRO-FURO[3,2-B] PYRROL-4(5H)-YL) DERIVATIVES II

(71) Applicant: GRÜNENTHAL GMBH, Aachen (DE)

(72) Inventors: Antonio Nardi, Herzogenrath (DE); Paul Ratcliffe, Aachen (DE); Tobias Craan, Aachen (DE); Torsten Hertrampf, Köln (DE); Bernhard Lesch, Aachen (DE); Henning Steinhagen, Schwalbach (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/693,975

(22) Filed: Apr. 23, 2015

(65) Prior Publication Data

US 2015/0307506 A1 Oct. 29, 2015

(30) Foreign Application Priority Data

Apr. 23, 2014 (EP) .................................. 14001458

(51) Int. Cl.
*C07D 491/048* (2006.01)
(52) U.S. Cl.
CPC ................. *C07D 491/048* (2013.01)
(58) Field of Classification Search
CPC .................................................. C07D 407/02
See application file for complete search history.

(56) References Cited

U.S. PATENT DOCUMENTS

| | | |
|---|---|---|
| 2007/0117785 A1 | 5/2007 | Butler et al. |
| 2010/0010009 A1 | 1/2010 | Quibell et al. |
| 2011/0009385 A1 | 1/2011 | Quibell et al. |

FOREIGN PATENT DOCUMENTS

| | | |
|---|---|---|
| WO | WO 2008/007127 A1 | 1/2008 |
| WO | 2009/112839 A1 | 9/2009 |

OTHER PUBLICATIONS

Vippagunta et al. (2001).*
U.S. Appl. No. 14/693,987, filed Apr. 23, 2015.*

Artursson et al, "Caco-2 and Emerging Alternatives for Prediction of Intestinal Drug Transport: A general Overview"; Drug Bioavailability 2003, 72-88.
Barclay et al., "Role of the cysteine protease cathepsin S in neuropathic hyperalgesia"; Pain, 2007, 130, 225-234.
Bossard et al., "Proteolytic Activity of Human Osteoclast Cathepsin K"; J. Biol. Chem. 1996, 271, 12517-12524.
Cheng et al., "Increased Expression of Elastolytic Cysteine Proteases, Cathepsins S and K, in the Neointima of Balloon-Injured Rat Carotid Arteries"; Am. J. Pathol., 2004, 164, 243-251.
Gupta et al.; "Cysteine cathepsin S as an immunomodulator target: present and future trends"; Expert Opin. Ther. Targets, 2008, 12, 291-299.
Hidalgo et al; "Characterization of the Human Colon Carcinoma Cell Line (Caco-2) as a Model System for Intestinal Epithelial Permeability"; Gastroenterology 1989, 96, 736-749.
Lee-Dutra et al,; "Cathepsin S inhibitors: 2004-2010"; Expert Opin. Ther. Patents, 2011, 21, 311-337.
Petermann et al.; "Lysosomal, cytoskeletal, and metabolic alterations in cardiomyopathy of cathepsin L knockout mice"; FASEB J. 2006, 20, 1266-1268, E587-E598.
Potts et al,; "Cathespin L-deficient mice exhibit abnormal skin and bone development and show increased resistance to osteoporosis following ovariectomy"; Int. J. Exp. Path. 2004, 85, 85-96.
Stypmann et al.; Dilated cardiomyopathy in mice deficient for the lysosomal cysteine peptidase cathepsin L; PNAS, 2002, 99, 6234-6239.
Sukhova et al.; "Expression of the elastolytic cathepsins S and K in human atheroma and regulation of their production in smooth muscle cells"; J. Clin. Invest., 1998, 102, 576-583.
Turk et al.; "Cysteine cathepsins: from structure, function and regulation to new frontiers" Biochim. Biophys. Acta, 2012. 1824, 68-88.
Wiener et al.; "Recent advances in the design of cathepsin S inhibitors"; Curr. Top. Med. Chem. 2010, 10, 717-732.
Yasuda et al.; "The role of cathepsins in osteoporosis and arthritis: Rationale for the design of new therapeutics"; Adv. Drug Deliv. Rev., 2005, 57, 973-993.
Zerbini et al.; "Odanacatib in postmenopausal women with low bone mineral density: a review of current clinical evidence"; Ther. Adv. Musculoskel. Dis. 2013, 5(4), 199-209.

* cited by examiner

*Primary Examiner* — Paul V Ward
(74) *Attorney, Agent, or Firm* — Norris McLaughlin & Marcus, P.A.

(57) ABSTRACT

The invention relates to amidic oxotetrahydro-2H-furo[3,2-b]pyrrol-4(5H)-yl) derivatives as dual CatS/K inhibitors exhibiting a pronounced CatK-inhibition, to pharmaceutical compositions containing these compounds and also to these compounds for use in the treatment and/or prophylaxis of pain and further diseases and/or disorders.

14 Claims, No Drawings

3-OXO-TETRAHYDRO-FURO[3,2-B]PYRROL-4(5H)-YL) DERIVATIVES II

This application claims priority of European Patent Application No. 14001458.0, filed Apr. 23, 2014, the entire contents of which is incorporated herein by reference.

FIELD OF THE INVENTION

The present invention relates to compounds that are dual inhibitors of the cysteine proteinases cathepsin S (CatS) and cathepsin K (CatK), pharmaceutical compositions containing said compounds, and their use in medical therapy. Such compounds are particularly useful for the therapeutic treatment of diseases which are at least partially modulated by CatS and CatK.

BACKGROUND OF THE INVENTION

Cysteine proteases represent a specific class of peptidases which bear a cysteine residue in the catalytic site of the enzyme. Many pathological disorders or diseases are the results of abnormal activity of cysteine proteases such as over expression or enhanced activation.

The cysteine cathepsins, e.g. cathepsins B, K, O, L, S, V and F, are a class of lysosomal protease enzymes which are implicated in a multitude of house-keeping roles, but also in various disease processes and disorders including inflammation, autoimmune diseases, e.g. rheumatoid arthritis, psoriasis, asthma, osteoarthritis, osteoporosis, tumors, coronary disease, atherosclerosis, and infectious diseases.

In contrast to the ubiquitously expressed housekeeping enzymes cathepsins B, O and L, cathepsin S (CatS) is highly expressed in antigen presenting cells of lymphatic tissues, primarily in dendritic cells, B cells and macrophages (Wiener et al., Curr. Top. Med. Chem., 2010, 10, 717). In the antigen presenting cells, CatS plays a major role in antigen presentation by degradation of invariant chain that is associated with the major histocompatibility class II complex.

There currently exists a major unmet need for safe orally administered medications for the treatment of inflammatory diseases such as rheumatoid arthritis, osteoarthritis, chronic obstructive pulmonary disease (COPD) and cardiovascular disease, which exhibit significant damage and remodeling of extracellular matrix (ECM).

Destruction of the ECM takes place through proteolysis of its elastin, collagen and proteoglycan constituents, which provide structure, elasticity and tensile strength to materials such as cartilage, bone, lung and vascular tissue.

US 2007/0117785 discloses inhibitors of CatS, supporting the use of CatS inhibitors for the treatment of certain allergic conditions, such as rheumatoid arthritis or psoriasis.

CatS has also been demonstrated to mediate a pronociceptive effect, thereby indicating that endogenous CatS released by peripheral macrophages may contribute to the maintenance of neuropathic hyperalgesia following nerve injury (Barclay et al., Pain, 2007, 130, 225).

CatK is predominantly expressed in osteoclasts (Yasuda et al., Adv. Drug Deliv. Rev., 2005, 57, 973). By cleavage of bone matrix proteins, CatK is involved in extracellular matrix metabolism necessary for normal bone growth and remodelling (Bossard et al., J. Biol. Chem. 1996, 271, 12517). Hence, inhibition of CatK should result in a reduction of osteoclast mediated bone resorption. The CatK inhibitor Odanacatib has been validated in humans for the treatment of osteoporosis (Zerbini and McClung, Ther. Adv. Musculoskel. Dis. 2013, 5(4), 199-209).

The proteolytic enzymes cathepsin S and cathepsin K are up-regulated under inflammatory conditions and have been implicated in the degradation of ECM components. For instance, CatK and CatS are found over-expressed in rheumatoid and osteoarthritic synovium. They have been shown to degrade collagen type-I and type-II, as well as aggrecan (a multidomain proteoglycan component of articular cartilage) respectively (Yasuda et al., Adv. Drug Deliv. Rev., 2005, 57, 973).

Besides destruction of articular cartilage, CatS and CatK demonstrate potent elastinolytic activity and are involved in a broad spectrum of pathological conditions associated with elastin degradation, such as COPD and cardiovascular disease. Both enzymes are readily secreted by macrophages and smooth muscle cells and have been shown to degrade elastins from bovine aorta and lung tissue. CatS and CatK are also responsible for the vascular tissue damage associated with chronic cardiovascular disease and vascular injury.

Further, CatS and CatK have been found to play a crucial role in in atherosclerotic lesion destabilization and eventually induction of atherosclerotic plaque rupture (Sukhova et al., J. Clin. Invest., 1998, 102, 576). CatS and CatK have also been associated with vascular remodeling and causing ECM damage during the development of atherosclerosis and vascular injury-induced neointimal formation (Cheng et al., Am. J. Pathol., 2004, 164, 243).

Thus, inhibition of CatS and CatK offer an attractive approach to prevent the tissue destruction underlying chronic inflammatory diseases such as rheumatoid arthritis, osteoarthritis, COPD and cardiovascular disease.

Since CatS and CatK appear to work in tandem and both are present in many chronic inflammatory diseases, a single compound possessing dual inhibitory activity would be a distinct advantage. There are presently no human therapeutic dual inhibitors. The use of dual CatS/K inhibitors for the treatment of conditions with inflammatory and joint-destructive components, such as rheumatoid arthritis has been suggested (Gupta et al. Expert Opin. Ther. Targets, 2008, 12, 291) and demonstrated in a collagen-induced murine arthritis model (Lee-Dutra et al., Expert Opin. Ther. Patents, 2011, 21, 311).

WO 2009/112839 A1 describes particular 6-(1S)-chloro-tetrahydrofuro[3,2-b]pyrrol-3-ones according to general formula (I*), exhibiting potent dual inhibition versus both human CatS and CatK:

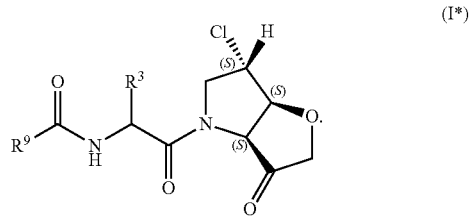

A major challenge in the development of such dual CatS/K inhibitors arises from selectivity issues towards other cathepsins. In particular, lysosomal, cytoskeletal and metabolic alterations in cardiomyopathy have been attributed to inhibition of cathepsin L (CatL) in CatL knock-out mice (Petermann et al., FASEB J. 2006, 20, 1266; Stypmann et al., PNAS, 2002, 99, 6234). Furthermore, it was shown that disruption of the cathepsin L gene leads to major abnormalities in skin and hair development and differentiation and alterations in trabecular bone deposition (Potts et al, Int. J. Exp. Path. 2004, 85, 85).

Structurally, the cathepsins K, L and S possess a high sequence homology (Lee-Dutra et al., Expert Opin. Ther. Patents 2011, 21, 311; Turk et al., Biochim. Biophys. Acta, 2012. 1824, 68). Therefore, a sufficient selectivity over ubiquitously expressed CatL to avoid the undesired effects associated with inhibition of CatL is regarded to be one of the prerequisites for therapeutic suitability of CatS inhibitors (Wiener et al., Curr. Top. Med. Chem. 2010, 10, 717), but will equally refer to dual CatS/CatK inhibitors.

SUMMARY OF THE INVENTION

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by both human CatS and human CatK.

Surprisingly, it has now been found that specific 6-(1S)-chlorotetrahydrofuro[3,2-b]pyrrol-3-ones not only exhibit potent dual inhibition of both human CatS and human CatK, but possess an significantly increased selectivity over CatL compared to the compounds known from WO 2009/112839 A1.

Moreover, the compounds according to the invention have surprisingly been found not to possess an equipotent dual inhibition versus both human CatS and CatK. Instead, they exhibit a more pronounced inhibition of human CatK, while still retaining high inhibition versus human CatS. As CatK is predominantly expressed in osteoclasts, compounds with an unbalanced dual inhibition mode on human CatS and CatK may be particularly suitable for the treatment of inflammatory bone diseases, such as rheumatoid arthritis or osteoarthritis.

The present invention therefore relates to a compound of general formula (I),

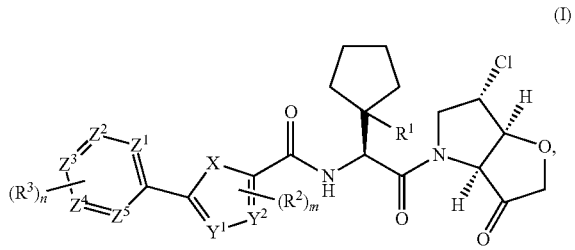

(I)

wherein
R$^1$ represents H or F,
X represents S or O;
Y$^1$ and Y$^2$ independently represents CH or N;
Z$^1$, Z$^2$, Z$^3$, Z$^4$ and Z$^5$ independently represents CH or N, with the proviso that 1, 2 or 3 of Z$^1$, Z$^2$, Z$^3$, Z$^4$ and Z$^5$ represent N;
m denotes 0, 1 or 2;
n denotes 0, 1, 2 or 3;
each R$^2$ and each R$^3$ is independently selected from the group consisting of F; Cl; Br; CN; CF$_3$; CF$_2$H; CFH$_2$; CF$_2$Cl; CFCl$_2$; C$_{1-4}$-alkyl; C(=O)—(C$_{1-4}$-alkyl); C(=O)—NH$_2$; C(=O)—N(H)(C$_{1-4}$-alkyl); C(=O)—N (C$_{1-4}$-alkyl)$_2$; OH; O—C$_{1-4}$-alkyl; OCF$_3$; OCF$_2$H; OCFH$_2$; OCF$_2$Cl; OCFCl$_2$; NH$_2$; N(H)(C$_{1-4}$-alkyl); N(C$_{1-4}$-alkyl)$_2$; N(H)—C(=O)—(C$_{1-4}$-alkyl); N(C$_{1-4}$-alkyl)-C(=O)—(C$_{1-4}$-alkyl); N(H)—S(=O)$_2$—(C$_{1-4}$-alkyl); N(H)—C(=O)—NH$_2$; N(H)—C(=O)—N(H) (C$_{1-4}$-alkyl); N(H)—C(=O)—N(C$_{1-4}$-alkyl)(C$_{1-4}$-alkyl); S—(C$_{1-4}$-alkyl); S(=O)—(C$_{1-4}$-alkyl); S(=O)$_2$—(C$_{1-4}$-alkyl); S(=O)$_2$—N(H)(C$_{1-4}$-alkyl); cyclopropyl; O-cyclopropyl; NH-cyclopropyl; N(H)—C(=O)-cyclopropyl; S(=O)-(cyclopropyl) and S(=O)$_2$-(cyclopropyl);
wherein the above-mentioned substituents C$_{1-4}$-alkyl and cyclopropyl, may in each case be unsubstituted or substituted one or more times by identical or different substituents, and the above-mentioned substituent C$_{1-4}$-alkyl may in each case be branched or unbranched;
in the form of an individual stereoisomer or a mixture thereof; in the form of a tautomer; of a free compound; of an N-oxide; or in the form of a solvate and/or of a physiologically acceptable salt.

The term "physiologically acceptable salt" preferably comprises in the sense of this invention a salt of at least one compound according to the present invention and at least one physiologically acceptable acid or base.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents.

The term "C$_{1-4}$-alkyl" comprise in the sense of this invention acyclic saturated aliphatic hydrocarbon residues, which can be respectively branched or unbranched and can be unsubstituted or can be mono- or polysubstituted, e.g. mono-, di- or trisubstituted, and which contain 1 to 6 carbon atoms, i.e. 1, 2, 3 or 4 carbon atoms. Preferred C$_{1-4}$-alkyl groups are selected from the group consisting of methyl, ethyl, n-propyl, 2-propyl, n-butyl, isobutyl, sec-butyl and tert-butyl.

In relation to the term "C$_{1-4}$-alkyl" the term "monosubstituted" or "polysubstituted" such as di- or tri-substituted refers in the sense of this invention, with respect to the corresponding groups, to the single substitution or multiple substitution, e.g. disubstitution or trisubstitution, of one or more hydrogen atoms each independently of one another by at least one substituent. The term "polysubstituted" such as di- or tri-substituted with respect to polysubstituted groups such as di- or tri-substituted groups includes the polysubstitution of these groups either on different or on the same atoms, for example trisubstituted on the same carbon atom, as in the case of CF$_3$ or CH$_2$CF$_3$ or at various points, as in the case of CH(OH)CHCl$_2$. The multiple substitution can be carried out using the same or using different substituents.

In relation to the terms "C$_{1-4}$-alkyl" and "cyclopropyl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; I; NO$_2$; CN; =O; =NH; =N(OH); =N(O—C$_{1-4}$-alkyl); CF$_3$; CF$_2$H; CFH$_2$; CF$_2$Cl; CFCl$_2$; C$_{1-4}$-alkyl; C(=O)—H; C(=O)—C$_{1-4}$-alkyl; C(=O)—OH; C(=O)—O—C$_{1-4}$-alkyl; C(=O)—N (H)(OH); C(=O)—NH$_2$; C(=O)—N(H)(C$_{1-4}$-alkyl); C(=O)—N(C$_{1-4}$-alkyl)$_2$; C(=N—OH)—H; C(=N—OH)—C$_{1-4}$-alkyl; C(=N—O—C$_{1-4}$-alkyl)-H; C(=N—O—C$_{1-4}$-alkyl)-C$_{1-4}$-alkyl; OH; OCF$_3$; OCF$_2$H; OCFH$_2$; OCF$_2$Cl; OCFCl$_2$; O—C$_{1-4}$-alkyl; O—C(=O)—C$_{1-4}$-alkyl;

O—C(=O)—O—C$_{1-4}$-alkyl; O—(C=O)—N(H)(C$_{1-4}$-alkyl); O—C(=O)—N(C$_{1-4}$-alkyl)$_2$; O—S(=O)$_2$—C$_{1-4}$-alkyl; O—S(=O)$_2$—OH; O—S(=O)$_2$—O—C$_{1-4}$-alkyl; O—S(=O)$_2$—NH$_2$; O—S(=O)$_2$—N(H)(C$_{1-4}$-alkyl); O—S(=O)$_2$—N(C$_{1-4}$-alkyl)$_2$; NH$_2$; N(H)(C$_{1-4}$-alkyl); N(C$_{1-4}$-alkyl)$_2$; N(H)—C(=O)—C$_{1-4}$-alkyl; N(H)—C(=O)—O—C$_{1-4}$-alkyl; N(H)—C(=O)—NH$_2$; N(H)—C(=O)—N(H)(C$_{1-4}$-alkyl); N(H)—C(=O)—N(C$_{1-4}$-alkyl)$_2$; N(C$_{1-4}$-alkyl)-C(=O)—C$_{1-4}$-alkyl; N(C$_{1-4}$-alkyl)-C(=O)—O—C$_{1-4}$-alkyl; N(C$_{1-4}$-alkyl)-C(=O)—NH$_2$; N(C$_{1-4}$-alkyl)-C(=O)—N(H)(C$_{1-4}$-alkyl); N(C$_{1-4}$-alkyl)-C(=O)—N(C$_{1-4}$-alkyl)$_2$; N(H)—S(=O)$_2$—OH; N(H)—S(=O)$_2$—C$_{1-4}$-alkyl; N(H)—S(=O)$_2$—O—C$_{1-4}$-alkyl; N(H)—S(=O)$_2$—NH$_2$; N(H)—S(=O)$_2$—N(H)(C$_{1-4}$-alkyl); N(H)—S(=O)$_2$—N(C$_{1-4}$-alkyl)$_2$; N(C$_{1-4}$-alkyl)-S(=O)$_2$—OH; N(C$_{1-4}$-alkyl)-S(=O)$_2$—C$_{1-4}$-alkyl; N(C$_{1-4}$-alkyl)-S(=O)$_2$—O—C$_{1-4}$-alkyl; N(C$_{1-4}$-alkyl)-S(=O)$_2$—NH$_2$; N(C$_{1-4}$-alkyl)S(=O)$_2$—N(H)(C$_{1-4}$-alkyl); N(C$_{1-4}$-alkyl)-S(=O)$_2$—N(C$_{1-4}$-alkyl)$_2$; SH; SCF$_3$; SCF$_2$H; SCFH$_2$; SCF$_2$Cl; SCFCl$_2$; S—C$_{1-4}$-alkyl; S(=O)—C$_{1-4}$-alkyl; S(=O)$_2$—C$_{1-4}$-alkyl; S(=O)$_2$—OH; S(=O)$_2$—O—C$_{1-4}$-alkyl; S(=O)$_2$—NH$_2$; S(=O)$_2$—N(H)(C$_{1-4}$-alkyl); S(=O)$_2$—N(C$_{1-4}$-alkyl)$_2$; C$_{3-10}$-cycloalkyl; 3 to 7 membered heterocyclyl; aryl or heteroaryl.

Preferred substituents of "C$_{1-4}$-alkyl" are selected from the group consisting of F; Cl; Br; CF$_3$; C(=O)—NH$_2$; C(=O)—N(H)(C$_{1-4}$-alkyl); C(=O)—N(C$_{1-6}$-alkyl)$_2$; C$_{3-6}$-cycloalkyl or 3 to 7 membered heterocyclyl; OH; O—C$_{1-4}$-alkyl; NH$_2$; N(H)(C$_{1-4}$-alkyl); N(C$_{1-4}$-alkyl)$_2$; N(H)—C(=O)—C$_{1-4}$-alkyl; N(H)—S(=O)$_2$—C$_{1-4}$-alkyl; N(C$_{1-4}$-alkyl)S(=O)$_2$—C$_{1-4}$-alkyl; N(H)—S(=O)$_2$—NH$_2$; SH; S—C$_{1-4}$-alkyl; S(=O)$_2$—C$_{1-4}$-alkyl and S(=O)$_2$—N(H)(C$_{1-4}$-alkyl).

Preferred substituents of "cycloalkyl" are selected from the group consisting of F; Cl; Br; CF$_3$; CN; =O; C$_{1-4}$-alkyl; C$_{3-6}$-cycloalkyl or 3 to 7 membered heterocyclyl; CHO; C(=O)—C$_{1-4}$-alkyl; CO$_2$H; C(=O)O—C$_{1-4}$-alkyl; CONH$_2$; C(=O)NH—C$_{1-4}$-alkyl; C(=O)N(C$_{1-4}$-alkyl)$_2$; OH; O—C$_{1-4}$-alkyl; OCF$_3$; O—C(=O)—C$_{1-4}$-alkyl; NH$_2$; NH—C$_{1-4}$-alkyl; N(C$_{1-4}$-alkyl)$_2$; NH—C(=O)—C$_{1-4}$-alkyl; SH; S—C$_{1-4}$-alkyl; SCF$_3$; S(=O)$_2$—C$_{1-4}$-alkyl; S(=O)$_2$OH; S(=O)$_2$O—C$_{1-4}$-alkyl and S(=O)$_2$—NH—C$_{1-4}$-alkyl.

The term "C$_{3-10}$-cycloalkyl" mean for the purposes of this invention cyclic aliphatic hydrocarbons containing 3, 4, 5, 6, 7, 8, 9 or 10 carbon atoms, respectively, wherein the hydrocarbons in each case can be saturated or unsaturated (but not aromatic), unsubstituted or mono- or polysubstituted. The cycloalkyl group can be bound to the respective superordinate general structure via any desired and possible ring member of the cycloalkyl group. The cycloalkyl group can also be condensed with further saturated, (partially) unsaturated, (hetero)cyclic, aromatic or heteroaromatic ring systems, i.e. with cycloalkyl, heterocyclyl, aryl or heteroaryl residues, which in each case can in turn be unsubstituted or mono- or polysubstituted. C$_{3-10}$-cycloalkyls can furthermore be singly or multiply bridged such as, for example, in the case of adamantyl, bicyclo[2.2.1]heptyl or bicyclo[2.2.2]octyl. Preferred C$_{3-10}$-cycloalkyl groups are selected from the group consisting of cyclopropyl, cyclobutyl, cyclopentyl, cyclohexyl, cycloheptyl, cyclooctyl, cyclononyl, cyclodecyl, adamantly, cyclopentenyl, cyclohexenyl, cycloheptenyl, cyclooctenyl,

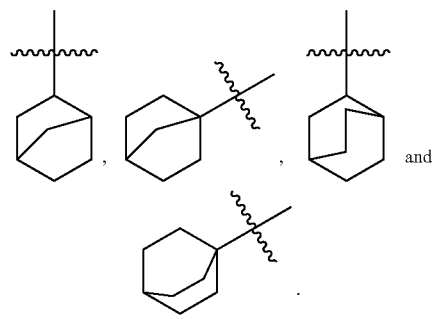
and

Particularly preferred C$_{3-10}$-cycloalkyl groups are C$_{3-6}$-cycloalkyl groups such as cyclopropyl, cyclobutyl, cyclopentyl, cyclohexyl, cyclopentenyl and cyclohexenyl, in particular cyclopropyl.

The terms "3 to 7-membered heterocyclyl" mean for the purposes of this invention heterocycloaliphatic saturated or unsaturated (but not aromatic) residues having 3 to 7, i.e. 3, 4, 5, 6 or 7 ring members, respectively, in which in each case at least one, if appropriate also two or three carbon atoms are replaced by a heteroatom or a heteroatom group each selected independently of one another from the group consisting of O, S, S(=O), S(=O)$_2$, N, NH and N(C$_{1-4}$-alkyl) such as N(CH$_3$), wherein the ring members can be unsubstituted or mono- or polysubstituted. The cycloalkyl groups can also be condensed with further saturated or (partially) unsaturated cycloalkyl or heterocyclyl, aromatic or heteroaromatic ring systems, which in each case can in turn be unsubstituted or mono- or polysubstituted. The heterocyclyl group can be bound to the superordinate general structure via any desired and possible ring member of the heterocycloaliphatic residue if not indicated otherwise.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further saturated or (partially) unsaturated cycloalkyl or heterocyclyl, aromatic or heteroaromatic ring systems, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5-, 6-, 8-, 9- or 10-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 10 ring members, wherein the ring system can be formed with further saturated or (partially) unsaturated cycloalkyl or heterocyclyl, aromatic or heteroaromatic ring systems, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

Within the scope of the present invention, the symbols

or --- used in the formulae denotes a link of a corresponding residue to the respective superordinate general structure.

In one embodiment of the first aspect of the invention, the compound according to general formula (I) is characterized in that $R^1$ is H.

In another embodiment of the first aspect of the invention, the compound according to general formula (I) is characterized in that $Y^1$ represents CH or N and $Y^2$ represents CH; or $Y^1$ represents CH and $Y^2$ represents CH or N.

In yet another embodiment of the first aspect of the invention, the compound according to general formula (I) is characterized in that X represents S.

Preferably, $R^1$ is H and X represents S, as given in formula (I-1):

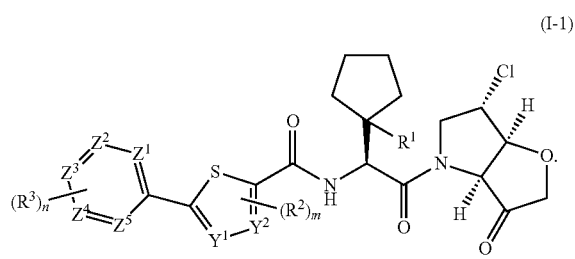

(I-1)

In yet another embodiment of the first aspect of the invention, the compound according to general formula (I) is characterized in that X represents S, $Y^1$ represents CH and $Y^2$ represents CH.

Preferably, $R^1$ is H, X represents S, $Y^1$ represents CH and $Y^2$ represents CH, as given in formula (I-2):

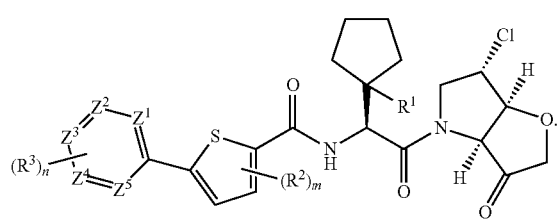

(I-2)

In yet another embodiment of the first aspect of the invention, the compound according to general formula (I) is characterized in that X represents S, $Y^1$ represents CH and $Y^2$ represents N.

Preferably, $R^1$ is H, X represents S, $Y^1$ represents CH and $Y^2$ represents N, as given in formula (I-3):

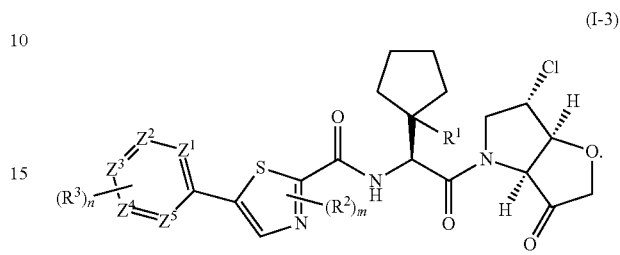

(I-3)

Yet another embodiment of the first aspect of the invention is characterized in that the compound according to general formula (I) is a compound according to general formula (Ia),

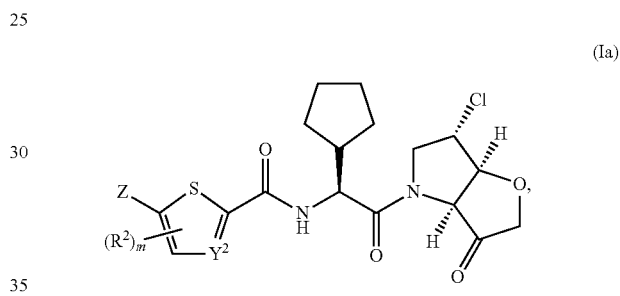

(Ia)

wherein Z represents

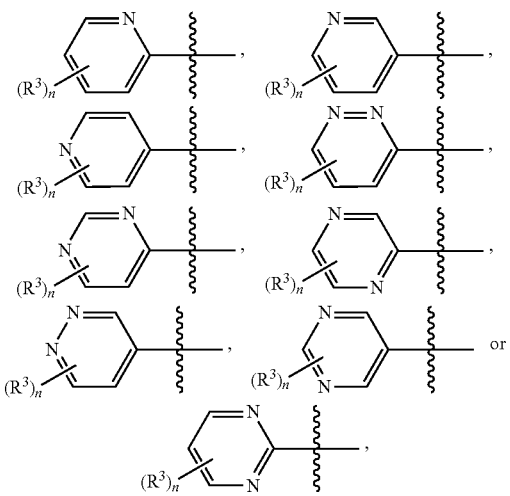

m denotes 0 or 1;
$Y^2$ represents N or CH;
$R^2$ is selected from the group consisting of F; Cl; Br; CN; $CF_3$; $CF_2H$; $CFH_2$; $CF_2Cl$; $CFCl_2$; $C_{1-4}$-alkyl; C(=O)—($C_{1-4}$-alkyl); C(=O)—$NH_2$; C(=O)—N(H)($C_{1-4}$-alkyl); C(=O)—N($C_{1-4}$-alkyl)$_2$; OH; O—$C_{1-4}$-alkyl; $OCF_3$; $OCF_2H$; $OCFH_2$; $OCF_2Cl$; $OCFCl_2$; $NH_2$; N(H)($C_{1-4}$-alkyl); N($C_{1-4}$-alkyl)$_2$; N(H)—C(=O)—($C_{1-4}$-alkyl);

N($C_{1-4}$-alkyl)-C(=O)—($C_{1-4}$-alkyl); N(H)—S(=O)$_2$—($C_{1-4}$-alkyl); N(H)—C(=O)—NH$_2$; N(H)—C(=O)—N(H)($C_{1-4}$-alkyl); N(H)—C(=O)—N($C_{1-4}$-alkyl)($C_{1-4}$-alkyl); S—($C_{1-4}$-alkyl); S(=O)—($C_{1-4}$-alkyl); S(=O)$_2$—($C_{1-4}$-alkyl); S(=O)$_2$—N(H)($C_{1-4}$-alkyl); cyclopropyl; O-cyclopropyl; NH-cyclopropyl; N(H)—C(=O)-cyclopropyl; S(=O)-(cyclopropyl) and S(=O)$_2$-(cyclopropyl);

n denotes 0, 1 or 2 and $R^3$ is independently selected from the group consisting of F; Cl; Br; CN; CF$_3$; CF$_2$H; CFH$_2$; CF$_2$Cl; CFCl$_2$; $C_{1-4}$-alkyl; C(=O)—($C_{1-4}$-alkyl); C(=O)—NH$_2$; C(=O)—N(H)($C_{1-4}$-alkyl); C(=O)—N($C_{1-4}$-alkyl)$_2$; OH; O—$C_{1-4}$-alkyl; OCF$_3$; OCF$_2$H; OCFH$_2$; OCF$_2$Cl; OCFCl$_2$; NH$_2$; N(H)($C_{1-4}$-alkyl); N($C_{1-4}$-alkyl)$_2$; N(H)—C(=O)—($C_{1-4}$-alkyl); N($C_{1-4}$-alkyl)-C(=O)—($C_{1-4}$-alkyl); N(H)—S(=O)$_2$—($C_{1-4}$-alkyl); N(H)—C(=O)—NH$_2$; N(H)—C(=O)—N(H)($C_{1-4}$-alkyl); N(H)—C(=O)—N($C_{1-4}$-alkyl)($C_{1-4}$-alkyl); S—($C_{1-4}$-alkyl); S(=O)—($C_{1-4}$-alkyl); S(=O)$_2$—($C_{1-4}$-alkyl); S(=O)$_2$—N(H)($C_{1-4}$-alkyl); cyclopropyl; O-cyclopropyl; NH-cyclopropyl; N(H)—C(=O)-cyclopropyl; S(=O)-(cyclopropyl) and S(=O)$_2$-(cyclopropyl).

Preferably, m denotes 0; $Y^2$ represents N or CH; n denotes 0, 1 or 2 and $R^3$ is independently selected from the group consisting of F; Cl; Br; CN; CF$_3$; CF$_2$H; CFH$_2$; CF$_2$Cl; CFCl$_2$; $C_{1-4}$-alkyl; C(=O)—($C_{1-4}$-alkyl); C(=O)—NH$_2$; C(=O)—N(H)($C_{1-4}$-alkyl); C(=O)—N($C_{1-4}$-alkyl)$_2$; OH; O—$C_{1-4}$-alkyl; OCF$_3$; OCF$_2$H; OCFH$_2$; OCF$_2$Cl; OCFCl$_2$; NH$_2$; N(H)($C_{1-4}$-alkyl); N($C_{1-4}$-alkyl)$_2$; N(H)—C(=O)—($C_{1-4}$-alkyl); N($C_{1-4}$-alkyl)-C(=O)—($C_{1-4}$-alkyl); N(H)—S(=O)$_2$—($C_{1-4}$-alkyl); N(H)—C(=O)—NH$_2$; N(H)—C(=O)—N(H)($C_{1-4}$-alkyl); N(H)—C(=O)—N($C_{1-4}$-alkyl)($C_{1-4}$-alkyl); S—($C_{1-4}$-alkyl); S(=O)—($C_{1-4}$-alkyl); S(=O)$_2$—($C_{1-4}$-alkyl); S(=O)$_2$—N(H)($C_{1-4}$-alkyl); cyclopropyl; O-cyclopropyl; NH-cyclopropyl; N(H)—C(=O)-cyclopropyl; S(=O)-(cyclopropyl) and S(=O)$_2$-(cyclopropyl).

In another embodiment of the first aspect of the invention, the compound according to general formula (Ia) is characterized in that m denotes 0; $Y^2$ represents N or CH; n denotes 0, 1 or 2 and $R^3$ is independently selected from the group consisting of F; Cl; CN; CF$_3$; CF$_2$H; CFH$_2$CH$_3$; CH$_2$CH$_3$; CH(CH$_3$)$_2$; C(=O)CH$_3$; C(=O)NH$_2$; C(=O)N(H)(CH$_3$); C(=O)N(CH$_3$)$_2$; OH; OCH$_3$; OCF$_3$; OCF$_2$H; OCFH$_2$; NH$_2$; N(H)(CH$_3$); N(CH$_3$)$_2$; N(H)—C(=O)CH$_3$; N(H)—S(=O)$_2$CH$_3$; S(=O)CH$_3$; S(=O)$_2$CH$_3$; S(=O)$_2$—N(H)(CH$_3$); cyclopropyl and O-cyclopropyl.

Preferably, m denotes 0; $Y^2$ represents CH; n denotes 0, 1 or 2 and $R^3$ is independently selected from the group consisting of F; Cl; CN; CF$_3$; CF$_2$H; CFH$_2$CH$_3$; CH$_2$CH$_3$; CH(CH$_3$)$_2$; C(=O)CH$_3$; C(=O)NH$_2$; C(=O)N(H)(CH$_3$); C(=O)N(CH$_3$)$_2$; OH; OCH$_3$; OCF$_3$; OCF$_2$H; OCFH$_2$; NH$_2$; N(H)(CH$_3$); N(CH$_3$)$_2$; N(H)—C(=O)CH$_3$; N(H)—S(=O)$_2$CH$_3$; S(=O)CH$_3$; S(=O)$_2$CH$_3$; S(=O)$_2$—N(H)(CH$_3$); cyclopropyl and O-cyclopropyl.

Yet preferably, m denotes 0; $Y^2$ represents N; n denotes 0, 1 or 2 and $R^3$ is independently selected from the group consisting of F; Cl; CN; CF$_3$; CF$_2$H; CFH$_2$CH$_3$; CH$_2$CH$_3$; CH(CH$_3$)$_2$; C(=O)CH$_3$; C(=O)NH$_2$; C(=O)N(H)(CH$_3$); C(=O)N(CH$_3$)$_2$; OH; OCH$_3$; OCF$_3$; OCF$_2$H; OCFH$_2$; NH$_2$; N(H)(CH$_3$); N(CH$_3$)$_2$; N(H)—C(=O)CH$_3$; N(H)—S(=O)$_2$CH$_3$; S(=O)CH$_3$; S(=O)$_2$CH$_3$; S(=O)$_2$—N(H)(CH$_3$); cyclopropyl and O-cyclopropyl.

In another embodiment of the first aspect of the invention, the compound according to general formula (Ia) is characterized in that m denotes 0; $Y^2$ represents N or CH; Z represents

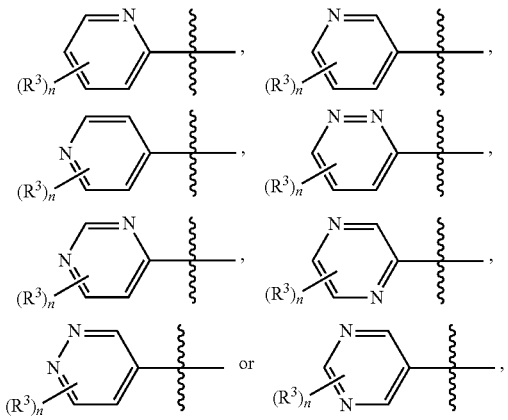

n denotes 0 or 1 and $R^3$ is independently selected from the group consisting of F; Cl; CN; CF$_3$; CF$_2$H; CFH$_2$CH$_3$; CH$_2$CH$_3$; CH(CH$_3$)$_2$; C(=O)CH$_3$; C(=O)NH$_2$; C(=O)N(H)(CH$_3$); C(=O)N(CH$_3$)$_2$; OH; OCH$_3$; OCF$_3$; OCF$_2$H; OCFH$_2$; NH$_2$; N(H)(CH$_3$); N(CH$_3$)$_2$; N(H)—C(=O)CH$_3$; N(H)—S(=O)$_2$CH$_3$; S(=O)CH$_3$; S(=O)$_2$CH$_3$; S(=O)$_2$—N(H)(CH$_3$); cyclopropyl and O-cyclopropyl.

In another embodiment of the first aspect of the invention, the compound according to general formula (Ia) is characterized in that m denotes 0; $Y^2$ represents N or CH; Z represents

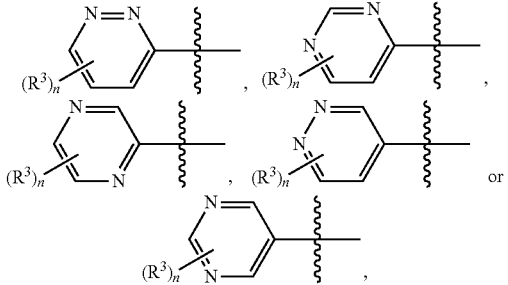

n denotes 0 or 1 and $R^3$ is independently selected from the group consisting of F; Cl; CN; CF$_3$; CF$_2$H; CFH$_2$CH$_3$; CH$_2$CH$_3$; CH(CH$_3$)$_2$; C(=O)CH$_3$; C(=O)NH$_2$; C(=O)N(H)(CH$_3$); C(=O)N(CH$_3$)$_2$; OH; OCH$_3$; OCF$_3$; OCF$_2$H; OCFH$_2$; NH$_2$; N(H)(CH$_3$); N(CH$_3$)$_2$; N(H)—C(=O)CH$_3$; N(H)—S(=O)$_2$CH$_3$; S(=O)CH$_3$; S(=O)$_2$CH$_3$; S(=O)$_2$—N(H)(CH$_3$); cyclopropyl and O-cyclopropyl.

Yet another embodiment of the first aspect of the invention is characterized in that the compound according to general formula (I) is a compound according to general formula (Ib),

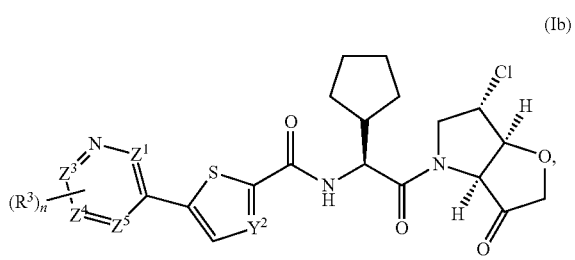

(Ib)

wherein $Y^2$ represents CH or N;
$Z^3$, $Z^4$ and $Z^5$ each represent CH and $Z^1$ represents N or
$Z^1$, $Z^4$ and $Z^5$ each represent CH and $Z^3$ represents N or
$Z^1$, $Z^3$ and $Z^5$ each represent CH and $Z^4$ represents N or
$Z^1$, $Z^3$ and $Z^4$ each represent CH and $Z^5$ represents N;
n denotes 0 or 1 and
$R^3$ is selected from the group consisting of F; Cl; CN; $CF_3$; $CF_2H$; $CFH_2$; $CH_3$; $OCH_3$ and $OCF_3$.

Preferably, the compound according to general formula (Ib) is characterized in that $Y^2$ represents CH.

Yet preferably, the compound according to general formula (Ib) is characterized in that $Y^2$ represents N.

In another embodiment of the first aspect of the invention, the compound according to general formula (Ib) is characterized in that $Y^2$ represents CH;
$Z^3$, $Z^4$ and $Z^5$ each represent CH and $Z^1$ represents N or
$Z^1$, $Z^4$ and $Z^5$ each represent CH and $Z^3$ represents N and n denotes 0.

Particularly preferred compounds according to the invention are selected from the group consisting of
1 N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridazin-3-yl)thiophene-2-carboxamide
2 N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridin-3-yl)thiophene-2-carboxamide
3 N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyrimidin-5-yl)thiophene-2-carboxamide
4 N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridazin-4-yl)thiophene-2-carboxamide
5 N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyrazin-2-yl)thiophene-2-carboxamide
6 N—((S)-2-((3aS,6S,6aS)-6-chloro-3-oxotetrahydro-2H-furo[3,2-b]pyrrol-4(5H)-yl)-1-cyclopentyl-2-oxoethyl)-5-(5-fluoropyridin-3-yl)thiophene-2-carboxamide
7 N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridazin-3-yl)thiazole-2-carboxamide
8 N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridine-4-yl)thiophene-2-carboxamide
optionally in the form of a single stereoisomer or a mixture of stereoisomers, in the form of the free compound and/or a physiologically acceptable salt or solvate thereof.

Compounds of general formula (I) are useful for the in vivo treatment or prevention of diseases in which participation of a cysteine protease is implicated.

Preferably, the compound of general formula (I) is a dual inhibitor of CatS and CatK (CatS/K inhibitors). More preferably, the compound of general formula (I) is a dual inhibitor of CatS and CatK with a pronounced effect on CatK (CatS/K inhibitors with preference for CatK).

The term "dual for CatS and CatK" is to be understood that the inhibitor is a potent inhibitor of both CatS and CatK. Furthermore, preference may be given to compounds according to the invention that cause at least a 50% inhibition at a concentration of 3 µM in a functional enzyme assay for both CatS as well as CatK, preferably less than 1000 nM for both CatS and CatK, particularly preferably less than 500 nM for both CatS and CatK, more preferably less than 400 nM for both CatS and CatK, even more preferably less than 300 nM for both CatS and CatK, even more preferably less than 200 nM for both CatS and CatK, even more preferably less than 150 nM for both CatS and CatK, even more preferably less than 100 nM for both CatS and CatK, and most preferably less than 50 nM for both CatS and CatK.

For these purposes functional enzyme assays using co-incubations of commercially available recombinant human cathepsines and respective fluorogenic substrates were conducted, as described hereinafter.

Preferably, the compounds according to present invention possess a high activity in both CatS enzyme assay and CatK enzyme assay, but exhibit a preference for the CatK enzyme assay. Preferably, the Ki value of CatK enzyme assay is significantly lower than the Ki value of CatS enzyme assay, while still retaining high inhibition in both CatS and CatK enzyme assays. Preferably the preference in activity for CatK over Cat S is at least 20 fold (relating to Ki(CatS)/Ki(CatK)≥20), preferably at least 50 fold (relating to Ki(CatS)/Ki(CatK)≥50), more preferably at least 100 fold (relating to Ki(CatS)/Ki(CatK)≥100), even more preferably at least 150 fold (relating to Ki(CatS)/Ki(CatK)≥150), and most preferably at least 200 fold (relating to Ki(CatS)/Ki(CatK)≥200), while in each case the compound still causes at least a 50% inhibition at a concentration of 1000 nM in a functional enzyme assay for CatS, preferably less than 500 nM for CatS, more preferably less than 400 nM for CatS, even more preferably less than 300 nM for CatS, even more preferably less than 200 nM for CatS, even more preferably less than 150 nM for CatS, even more preferably less than 100 nM for CatS, and most preferably less than 50 nM for CatS.

Furthermore, preference may be given to compounds according to the invention that do not inhibit CatL significantly. This means that the compounds cause preferably less than 50% inhibition at a concentration of 31.6 µM in a functional CatL enzyme assay.

Additionally, the compounds according to present invention exhibit a significant selectivity for both CatS as well as CatK over CatL. Preferably, the compounds possess a selectivity to CatS and to CatK over CatL of at least 100 (Ki(CatL)/Ki(CatK)>100 and Ki(CatL)/Ki(CatS)>100), preferably of at least 250 (Ki(CatL)/Ki(CatK)>250 and Ki(CatL)/Ki(CatS)>250), more preferably of at least 500 (Ki(CatL)/Ki(CatK)>500 and Ki(CatL)/Ki(CatS)>500) and most preferably of at least 1000 (Ki(CatL)/Ki(CatK)>1000 and Ki(CatL)/Ki(CatS)>1000).

Furthermore, preference may be given to compounds according to the invention that do not inhibit CatB significantly. This means that the compounds cause preferably less than 50% inhibition at a concentration of 31.6 µM in a functional CatB enzyme assay. Additionally, the compounds according to present invention exhibit a significant selectivity for both CatS as well as CatK over CatB. Preferably, the compounds possess a selectivity to CatS and to CatK over CatB of at least 100 (Ki(CatB)/Ki(CatK)>100 and Ki(CatB)/Ki(CatS)>100), preferably of at least 250 (Ki(CatB)/Ki(CatK)>250 and Ki(CatB)/Ki(CatS)>250), more preferably of at least 500 (Ki(CatB)/Ki(CatK)>500 and Ki(CatB)/Ki (CatS)>500) and most preferably of at least 1000 (Ki(CatB)/Ki(CatK)>1000 and Ki(CatB)/Ki(CatS)>1000).

The present invention further relates to a compound according to the present invention for modulation of both CatS and CatK, preferably for use in inhibition of CatS and CatK activity. The present invention therefore further relates to a compound according to the present invention for the prophylaxis and/or treatment of disorders and/or diseases which are mediated, at least in part, by both CatS and CatK without the inhibition of CatL and/or CatB. The present invention even further relates to a compound according to the present invention for the prophylaxis and/or treatment of disorders and/or diseases which are mediated, at least in part, by both CatS and CatK with a pronounced mediation by CatK without the inhibition of CatL and/or CatB.

According to a further aspect of the invention, there is provided the use of a compound according to the present invention in the preparation of a medicament for preventing or treating diseases in which the disease pathology may be modified by inhibiting a CatS and/or CatK.

In another aspect of the present invention, the invention therefore also provides pharmaceutical compositions, containing at least one compound according to the invention and optionally one or more suitable, pharmaceutically compatible auxiliaries and/or, if appropriate, one or more further pharmacologically active compounds.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one compound according to the invention, if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective compound according to the invention also in a delayed manner.

The pharmaceutical compositions according to the invention are prepared with the aid of conventional means, devices, methods and process known in the art. The amount to be administered to the patient of the respective compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

In the normal physiological process certain cysteine proteases function in the protein degradation in animals, including humans, e.g. in the degradation of connective tissue. Elevated levels of these cysteine proteases in the body may result in pathological conditions leading to disease. CatS and CatK are believed to be involved in a variety of diseases or disorders in mammals such as humans. These include pain (in particular chronic pain, inflammatory pain, mixed pain), inflammatory diseases and bone/cartilage preservation disorders.

Particularly useful are dual CatS and CatK (CatS/K) inhibitors for the treatment of rheumatoid arthritis (RA), osteoarthritis(OA), chronic obstructive pulmonary disease (COPD), atherosclerosis and cardiovascular diseases which exhibit significant damage and remodeling of extracellular matrix (ECM) and chronic pain.

Another embodiment of the present invention is at least one compound according the present invention for the treatment and/or prophylaxis of one or more disorders selected from the group consisting of nociceptive pain, neuropathic pain; erosive osteoarthritis (EO), in particular erosive osteoarthritis of the hand; Sjögren's Syndrom; rheumatoid arthritis (RA); psoriatic arthrithis (PsA), Psoriasis, Spondylarthritis, in particular ankylosing spondylitis; osteoporosis; Complex Regional Pain Syndrome (in particular CRPS I); Lupus erythematodes (SLE); Lupus nephritis; asthma; multiple sclerosis (MS); diabetes; chronic obstructive pulmonary disease (COPD), in particular COPD subpopoulation with osteoporosis; and asthma, in particular severe asthma subpopoulation with osteoporosis.

Another embodiment of the present invention therefore relates to use of at least one compound according to the present invention for the preparation of a pharmaceutical composition for the treatment and/or prophylaxis of one or more disorders or diseases, particularly selected from the group consisting of nociceptive pain, neuropathic pain; erosive osteoarthritis (EO), in particular erosive osteoarthritis of the hand; Sjögren's Syndrom; rheumatoid arthritis (RA); psoriatic arthrithis (PsA), Psoriasis, Spondylarthritis, in particular ankylosing spondylitis; osteoporosis; Complex Regional Pain Syndrome (in particular CRPS I); Lupus erythematodes (SLE); Lupus nephritis; asthma; multiple sclerosis (MS); diabetes; chronic obstructive pulmonary disease (COPD), in particular COPD subpopulation with osteoporosis; and asthma, in particular severe asthma subpopoulation with osteoporosis.

Another aspect of the present invention is a method of treatment and/or prophylaxis of disorders and/or diseases in a mammal, preferably of disorders and/or diseases selected from the group consisting of nociceptive pain, neuropathic pain; erosive osteoarthritis (EO), in particular erosive osteoarthritis of the hand; Sjögren's Syndrom; rheumatoid arthritis (RA); psoriatic arthrithis (PsA), Psoriasis, Spondylarthritis, in particular ankylosing spondylitis; osteoporosis; Complex Regional Pain Syndrome (in particular CRPS I); Lupus erythematodes (SLE); Lupus nephritis; asthma; multiple sclerosis (MS); diabetes; chronic obstructive pulmonary disease (COPD), in particular COPD subpopulation with osteoporosis; and asthma, in particular severe asthma subpopulation with osteoporosis.

All preferred embodiments of the first aspect of the invention are preferred vice versa for the other aspects and embodiments.

EXAMPLES

The compounds according to the invention can be prepared in the manner described below. The following examples further illustrate the invention but are not to be construed as limiting its scope.

All starting materials which are not explicitly described were either commercially available (the details of suppliers such as for example Acros, Avocado, Aldrich, Apollo, Bachem, Fluka, FluoroChem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington DC, US, respectively, for example) or the synthesis thereof has already been described precisely in the specialist literature (experimental guidelines can be found in the Reaxys® Database of Elsevier, Amsterdam, NL or the SciFinder® Database of the ACS, Washington DC, US, respectively, for example) or can be prepared using the conventional methods known to the person skilled in the art.

All reactions were conducted under nitrogen unless stated otherwise and monitored by TLC on silica gel coated glass plates or aluminium sheets. Flash column chromatography was performed on pre-packed silica gel columns (GraceResolve™) using the indicated solvents mixtures. All solvents were used without prior drying. Dry solvents were dried on molecular sieves (4A).

The NMR spectra were determined in DMSO-$d_6$ solutions, using a Bruker 400-UltraShield. Spectra are reported in δ units (ppm) and J values (Hz) with Me$_4$Si as the internal standard.

Acid HPLC analyses were conducted using an Agilent system, column: Waters XSelect (C18, 50×2.1 mm, 3.5µ), flow: 0.8 ml/min, column temp: 35° C., Eluent A: 0.1% Formic acid in acetonitrile, Eluent B: 0.1% Formic acid in water, lin. gradient: t=0 min 2% A, t=3.5 min 98% A, t=6 min 98% A, detection: DAD (220-320 nm), detection: MSD (ESI pos/neg) mass range: 100-800.

Basic HPLC analyses were conducted using an Agilent system, column: Waters XSelect (C18, 50×2.1 mm, 3.5µ), flow: 0.8 ml/min, column temp: 35° C., Eluent A: 95% acetonitrile+5% 10 mM NH$_4$HCO$_3$ in water, Eluent B: 10 mM NH$_4$HCO$_3$ in water (pH=9.0), lin. gradient: t=0 min 2% A, t=3.5 min 98% A, t=6 min 98% A, detection: DAD (220-320 nm), detection: MSD (ESI pos/neg) mass range: 100-800.

The indication "equivalents" ("eq." or "eq" or "equiv.") means molar equivalents, "RT" or "rt" means RTT (23±7° C.), "M" are indications of concentration in mol/l, "aq." means aqueous, "sat." means saturated, "sol." means solution, "conc." means concentrated. The mixing ratios of solvents are usually stated in the volume/volume ratio.

Further Abbreviations:

DME=1,2-dimethoxyethane; DCM=dichloromethane; DMF=N,N-Dimethylformamide; DMP=Dess-Martin periodinane; EDCI: N-(3-dimethylaminopropyl)-N'-ethylcarbodiimide hydrochloride; Et$_2$O=diethyl ether; EtOAc=ethyl acetate; FC=flash chromatography; h=hour(s); HOAt=1-hydroxy-7-azabenzotriazole; MeCN=acetonitrile; MeOH=methanol; RT=room temperature; NEt$_3$=triethylamine; THF=tetrahydrofuran.

INT-1 was prepared analogously to synthetic methods known from WO2009/112839.

Example 1

N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridazin-3-yl)thiophene-2-carboxamide

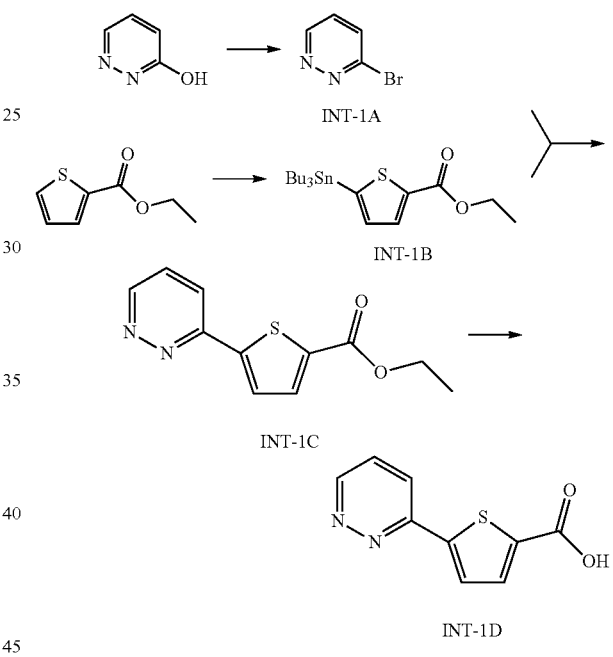

(i) Phosphorous oxybromide (158 g, 552 mmol) was heated to 80° C. under mechanical stirring until molten. 3-Hydroxypyridazine (30.5 g, 317 mmol) was added in one portion to the orange liquid, which afforded immediately a yellow, then a black solid. This was heated to 120° C. and left at this temperature for 3 h. After cooling to 0° C., small portions of ice water (in total: 300 mL) were slowly added and an exothermic reaction was observed (white smoke). During stirring, some solids did not dissolve, 2N aqueous NaOH (180 mL) was added at RT and stirred for 45 min until all solids were dissolved. The dark red/brown solution was poured into a mechanically stirred ice/water bath, which contained 2 N aqueous NaOH solution (910 mL). The internal temperature was kept below 25° C. during the addition. The pH was adjusted to ~9.5 by addition of 2 N aqueous NaOH (50 mL). The brown solution was extracted with DCM (5×250 mL). The combined yellow organic layer was dried over Na$_2$SO$_4$, filtered and concentrated in vacuo to obtain a grey/brown solid. The crude material was coated on silica (98 g) and filtered with heptane/EtOAc (1:1) over a plug of silica (200 g). Product containing fractions were combined and concentrated in vacuo to afford INT-1A (34.7 g 216 mmol, 69%) as a green/grey solid. GCMS: >99% pure.

(ii) Diisopropylamine (21.8 g, 215 mmol, 30.4 mL) was dissolved in dry THF (200 mL) and cooled to −78° C. under N₂. A solution of n-butyllithium (1.6M in hexanes, 215 mmol, 134 mL) was added drop wise. The mixture was allowed to warm to 0° C. and stirred for 30 min. The solution was cooled to −78° C. and a solution of ethyl thiophene-2-carboxylate (33.6 g, 215 mmol, 29.0 mL) in dry THF (50 mL) was added drop wise. The mixture was stirred at −78° C. for 1 h. A solution of tributyltinchloride (70.0 g, 215 mmol, 58.3 mL) in dry THF (50 mL) was added dropwise and the solution was stirred at −78° C. for 1 h, then allowed to warm up to RT and stirred for 1 h. The mixture was poured into 1 L aqueous saturated NH₄Cl and extracted with EtOAc (2×750 mL). The combined organic layer was dried over Na₂SO₄ and concentrated in vacuo to obtain a brown oil. Filtration over silica (~500 g, eluted with EtOAc/heptane 1:19) afforded INT-1B (86.8 g, 195 mmol, 91%) as a clear orange/brown solution.

(iii) A solution of INT-1A (28.2 g, 177 mmol) and INT-1B (86.8 g, 195 mmol) was degassed with Ar. CsF (81.0 g, 532 mmol), CuCl (2.28 g, 23.0 mmol) and PdCl₂(dppf) (6.96 g, 9.51 mmol) were added and the mixture was heated at 100° C. for 3 h. A solution of KF (25.0 g, 430 mmol) in 200 mL of water was added and the mixture was stirred vigorously for 3 h. The mixture was filtered over celite, rinsed with EtOAc (3×400 mL). The filtrate was diluted with aqueous saturated NaHCO₃ (500 mL) and water (500 mL). The layers were separated, the aqueous layer was extracted with EtOAc (750 mL). The combined organic layer was washed with brine (2×1 L), dried over Na₂SO₄ and concentrated in vacuo. The aqueous layer was divided in three 1 L portions, which were extracted with EtOAc (2×500 mL). The combined organic layer was dried over Na₂SO₄ and concentrated in vacuo and combined with the previous organic fraction. The product was purified by gravity column chromatography (~1 kg of silica, product loaded on Isolute, eluted with 5 L (EtOAc/heptane 1:4), 4 L (EtOAc/heptane 2:3), 4 L (EtOAc/heptane 3:2), 5 L (EtOAc/heptane 4:1), then pure EtOAc) to obtain INT-1C (15.6 g, 66.4 mmol, 38%) as a yellow solid. LCMS: calculated for [M+H]⁺=235.05, found 235.1.

(iv) LiOH.H₂O (5.70 g, 136 mmol) was added to a suspension of INT-1C (15.6 g, 66.4 mmol) in THF (200 mL) and water (150 mL). The mixture was heated to 65° C. for 1 h. The mixture was concentrated in vacuo. The residue was acidified to pH 3-4 (range) using aqueous 2M HCl (~70 mL). To this isopropyl alcohol (100 mL) was added. The solids were filtered off and washed with Et₂O, dried in vacuo to obtain INT-1D (13.1 g, 63.5 mmol, 96%) as a yellow solid. LCMS: calculated for [M+H]⁺=207.01, found 207.2.

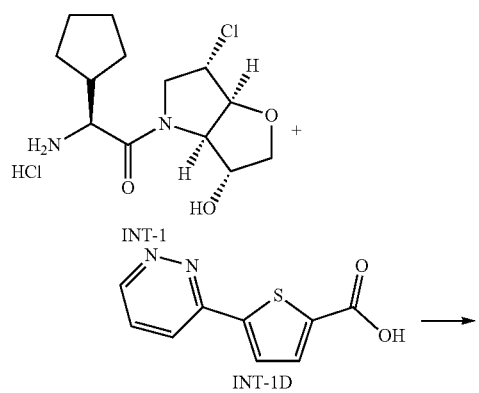

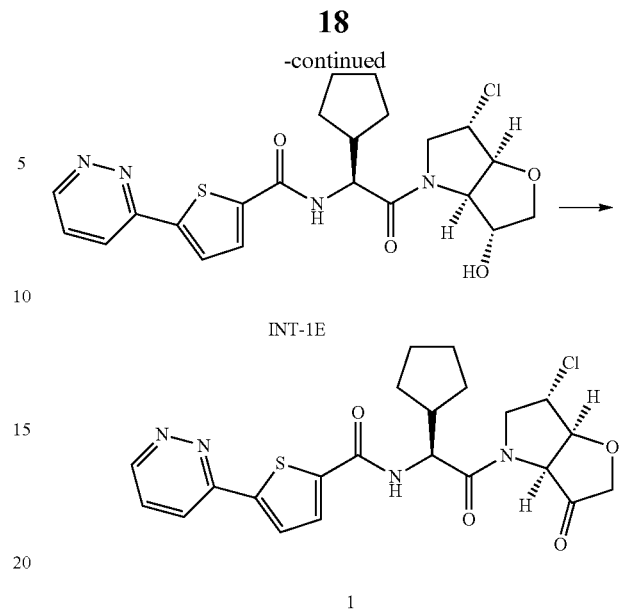

(v) A suspension of INT-1 (0.180 g, 0.553 mmol), INT-1D (0.114 g, 0.553 mmol), EDCI (0.127 g, 0.663 mmol), NEt₃ (0.269 mL, 1.94 mmol) and HOAt (0.0075 g, 0.055 mmol) in DMF (2 mL) was stirred at RT for 16 h (TLC, EtOAc/heptane 9:1). The mixture was diluted with aqueous saturated NaHCO₃ (10 mL) and extracted with EtOAc (3×10 mL). The combined organic layer was washed with brine (10 mL), dried over Na₂SO₄ and concentrated in vacuo. Flash chromatography (EtOAc/heptane 1:9 to 1:0) afforded INT-1E (0.128 g, 0.268 mmol, 49%). LCMS: calculated for [M+H]⁺=477.14, found 477.2.

(vi) DMP (0.228 g, 0.537 mmol) was added to a solution of INT-1E (0.128 g, 0.268 mmol) in DCM (4 mL). The mixture was stirred at RT for 18 h. An aqueous solution of Na₂S₂O₃ (10%, 10 mL) was added and the mixture was stirred vigorously for 30 min. An aqueous saturated solution of NaHCO₃ (10 mL) was added and the layers were separated. The aqueous layer was extracted with DCM (10 mL). The combined organic layer was dried over Na₂SO₄. The filtrate was concentrated in vacuo. Purified by basic preparative HPLC (C18, MeCN (1% 10 mM NH₄HCO₃), 10 mM NH₄HCO₃ in H₂O) and lyophilized to obtain 1 (0.100 g, 0.211 mmol, 78%). LCMS: calculated for [M+H]⁺=475.12, found 475.2. ¹H NMR (400 MHz, DMSO-d₆) as a mixture of hydrates and rotamers δ 9.25-8.90 (m, 2H), 8.41-8.22 (m, 1H), 8.21-7.93 (m, 2H), 7.90-7.71 (m, 1H), 6.77 (s, 0.48H), 6.49 (s, 0.33H), 6.41 (s, 0.48H), 5.78 (s, 0.33H), 5.21-3.46 (m, 8H), 2.48-2.30 (m, 1H), 1.90-1.07 (m, 8H) ppm.

Example 2

N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridin-3-yl)thiophene-2-carboxamide

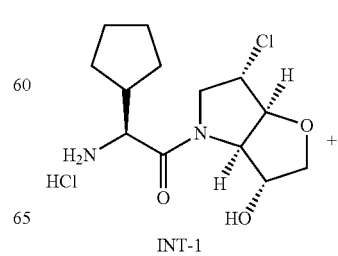

19

-continued

20

Example 3

N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyrimidin-5-yl)thiophene-2-carboxamide

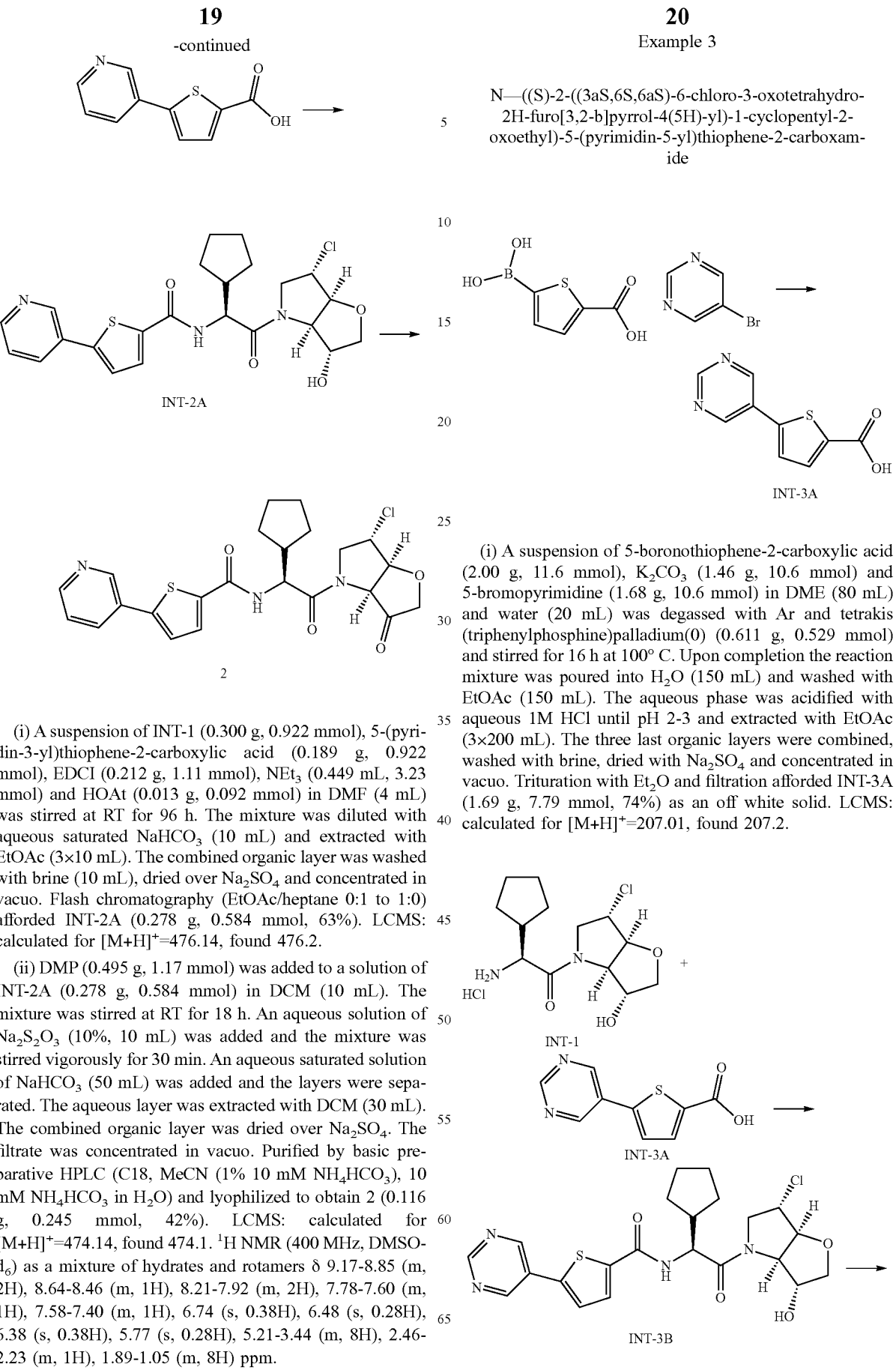

(i) A suspension of INT-1 (0.300 g, 0.922 mmol), 5-(pyridin-3-yl)thiophene-2-carboxylic acid (0.189 g, 0.922 mmol), EDCI (0.212 g, 1.11 mmol), NEt₃ (0.449 mL, 3.23 mmol) and HOAt (0.013 g, 0.092 mmol) in DMF (4 mL) was stirred at RT for 96 h. The mixture was diluted with aqueous saturated NaHCO₃ (10 mL) and extracted with EtOAc (3×10 mL). The combined organic layer was washed with brine (10 mL), dried over Na₂SO₄ and concentrated in vacuo. Flash chromatography (EtOAc/heptane 0:1 to 1:0) afforded INT-2A (0.278 g, 0.584 mmol, 63%). LCMS: calculated for [M+H]⁺=476.14, found 476.2.

(ii) DMP (0.495 g, 1.17 mmol) was added to a solution of INT-2A (0.278 g, 0.584 mmol) in DCM (10 mL). The mixture was stirred at RT for 18 h. An aqueous solution of Na₂S₂O₃ (10%, 10 mL) was added and the mixture was stirred vigorously for 30 min. An aqueous saturated solution of NaHCO₃ (50 mL) was added and the layers were separated. The aqueous layer was extracted with DCM (30 mL). The combined organic layer was dried over Na₂SO₄. The filtrate was concentrated in vacuo. Purified by basic preparative HPLC (C18, MeCN (1% 10 mM NH₄HCO₃), 10 mM NH₄HCO₃ in H₂O) and lyophilized to obtain 2 (0.116 g, 0.245 mmol, 42%). LCMS: calculated for [M+H]⁺=474.14, found 474.1. ¹H NMR (400 MHz, DMSO-d₆) as a mixture of hydrates and rotamers δ 9.17-8.85 (m, 2H), 8.64-8.46 (m, 1H), 8.21-7.92 (m, 2H), 7.78-7.60 (m, 1H), 7.58-7.40 (m, 1H), 6.74 (s, 0.38H), 6.48 (s, 0.28H), 6.38 (s, 0.38H), 5.77 (s, 0.28H), 5.21-3.44 (m, 8H), 2.46-2.23 (m, 1H), 1.89-1.05 (m, 8H) ppm.

(i) A suspension of 5-boronothiophene-2-carboxylic acid (2.00 g, 11.6 mmol), K₂CO₃ (1.46 g, 10.6 mmol) and 5-bromopyrimidine (1.68 g, 10.6 mmol) in DME (80 mL) and water (20 mL) was degassed with Ar and tetrakis(triphenylphosphine)palladium(0) (0.611 g, 0.529 mmol) and stirred for 16 h at 100° C. Upon completion the reaction mixture was poured into H₂O (150 mL) and washed with EtOAc (150 mL). The aqueous phase was acidified with aqueous 1M HCl until pH 2-3 and extracted with EtOAc (3×200 mL). The three last organic layers were combined, washed with brine, dried with Na₂SO₄ and concentrated in vacuo. Trituration with Et₂O and filtration afforded INT-3A (1.69 g, 7.79 mmol, 74%) as an off white solid. LCMS: calculated for [M+H]⁺=207.01, found 207.2.

-continued

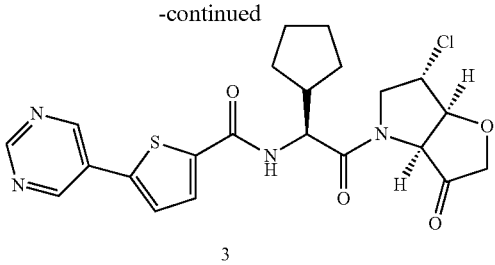

3

(ii) A suspension of INT-1 (0.300 g, 0.922 mmol), INT-3A (0.190 g, 0.922 mmol), EDCI (0.212 g, 1.11 mmol), NEt₃ (0.449 mL, 3.23 mmol) and HOAt (0.013 g, 0.092 mmol) in DMF (4 mL) was stirred at RT for 96 h. The mixture was diluted with aqueous saturated NaHCO₃ (10 mL) and extracted with EtOAc (3×10 mL). The combined organic layer was washed with brine (10 mL), dried over Na₂SO₄ and concentrated in vacuo. Flash chromatography (EtOAc/heptane 0:1 to 1:0) afforded INT-3B (0.269 g, 0.564 mmol, 61%). LCMS: calculated for [M+H]⁺=477.14, found 477.2.

(iii) DMP (0.478 g, 1.13 mmol) was added to a solution of INT-3B (0.269 g, 0.564 mmol) in DCM (10 mL). The mixture was stirred at RT for 18 h. An aqueous solution of Na₂S₂O₃ (10%, 10 mL) was added and the mixture was stirred vigorously for 30 min. An aqueous saturated solution of NaHCO₃ (50 mL) was added and the layers were separated. The aqueous layer was extracted with DCM (30 mL). The combined organic layer was dried over Na₂SO₄. The filtrate was concentrated in vacuo. Purified by basic preparative HPLC (C18, MeCN (1% 10 mM NH₄HCO₃), 10 mM NH₄HCO₃ in H₂O) and lyophilized to obtain 3 (0.136 g, 0.286 mmol, 51%). LCMS: calculated for [M+H]⁺=475.12, found 475.1. ¹H NMR (400 MHz, DMSO-d₆) as a mixture of hydrates and rotamers δ 9.20-9.14 (m, 3H), 9.13-8.96 (m, 1H), 8.40-8.01 (m, 1H), 7.82-7.74 (m, 1H), 6.73 (s, 0.28H), 6.48 (s, 0.21H), 6.35 (s, 0.28H), 5.77 (s, 0.21H), 5.21-3.44 (m, 8H), 2.48-2.25 (m, 1H), 1.85-1.08 (m, 8H) ppm.

Example 4

N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridazin-4-yl)thiophene-2-carboxamide

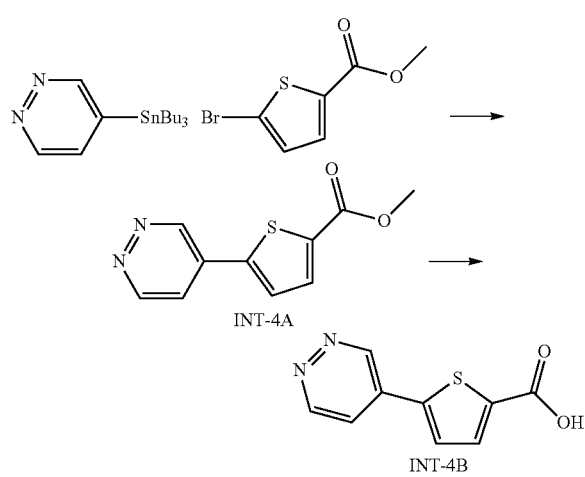

(i) A mixture of the methyl 5-bromothiophene-2-carboxylate (0.350 g, 1.58 mmol), CsF (0.480 g, 3.16 mmol) and the 4-(tributylstannyl)pyridazine (0.642 g, 1.74 mmol) was dissolved in DMF (4 mL). Tetrakis(triphenylphosphine)palladium(0) (0.183 g, 0.158 mmol) and CuI (0.060 g, 0.32 mmol) were added and the mixture was degassed with Ar. The mixture was stirred at 80° C. for 2 h and diluted with DCM (50 mL) and H₂O (20 mL). The organic layer was dried with Na₂SO₄ and filtered through celite. The filter cake was washed with DCM/EtOAc (100 mL, 1:1). The mixture was concentrated in vacuo and the residue triturated with Et₂O. The solvent was filtered off affording INT-4A (0.396 g, 1.71 mmol, quantitative) as a white solid. LCMS: calculated for [M+H]⁺=221.03, found 221.0.

(ii) To a mixture of INT-4A (0.396 g, 1.80 mmol) in THF (20 mL) and water (20 mL) was added LiOH.H₂O (0.226 g, 5.39 mmol). The reaction mixture was stirred at RT for 16 h. The mixture was concentrated in vacuo. Reversed phase chromatography (MeCN/H₂O (+0.1% HCOOH) 1:19 to 1:0) afforded INT-4B (0.465 g, 2.08 mmol, quantitative) as an off-white solid. LCMS: calculated for [M+H]⁺=207.01, found 207.0.

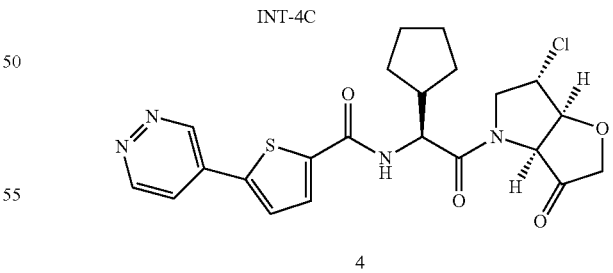

4

(iii) A suspension of INT-1 (0.276 g, 0.849 mmol), INT-4B (0.175 g, 0.849 mmol), EDCI (0.195 g, 1.02 mmol), NEt₃ (0.413 mL, 2.97 mmol) and HOAt (0.012 g, 0.085 mmol) in DMF (4 mL) was stirred at RT for 72 h. The mixture was diluted with aqueous saturated NaHCO₃ (10 mL) and extracted with EtOAc (3×10 mL). The combined organic layer was washed with brine (10 mL), dried over Na₂SO₄ and concentrated in vacuo. Flash chromatography (MeCN/EtOAc 0:1 to 1:0) afforded INT-4C (0.294 g, 0.616 mmol, 73%). LCMS: calculated for [M+H]$^+$=477.14, found 477.2.

(iv) DMP (0.523 g, 1.23 mmol) was added to a solution of INT-4C (0.294 g, 0.616 mmol) in DCM (10 mL). The mixture was stirred at RT for 18 h. An aqueous solution of Na$_2$S$_2$O$_3$ (10%, 5 mL) was added and the mixture was stirred vigorously for 30 min. An aqueous saturated solution of NaHCO$_3$ (10 mL) was added and the layers were separated. The aqueous layer was extracted with DCM (10 mL). The combined organic layer was dried over Na$_2$SO$_4$. The filtrate was concentrated in vacuo. Purified by basic preparative HPLC (C18, MeCN (1% 10 mM NH$_4$HCO$_3$), 10 mM NH$_4$HCO$_3$ in H$_2$O) and lyophilized to obtain 4 (0.146 g, 0.307 mmol, 50%). LCMS: calculated for [M+H]$^+$=475.12, found 475.1. $^1$H NMR (400 MHz, DMSO-d$_6$) as a mixture of hydrates and rotamers δ 9.70-9.60 (m, 1H), 9.30-9.21 (m, 1H), 9.21-8.98 (m, 1H), 8.50-7.87 (m, 3H), 6.72 (s, 0.39H), 6.48 (s, 0.31H), 6.32 (s, 0.39H), 5.76 (s, 0.31H), 5.19-3.43 (m, 8H), 2.48-2.26 (m, 1H), 1.89-1.05 (m, 8H) ppm.

Example 5

N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyrazin-2-yl)thiophene-2-carboxamide

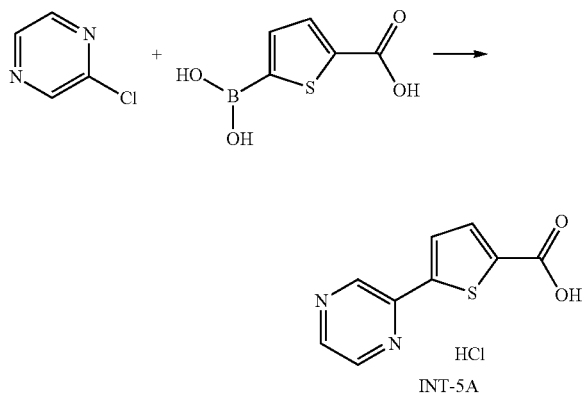

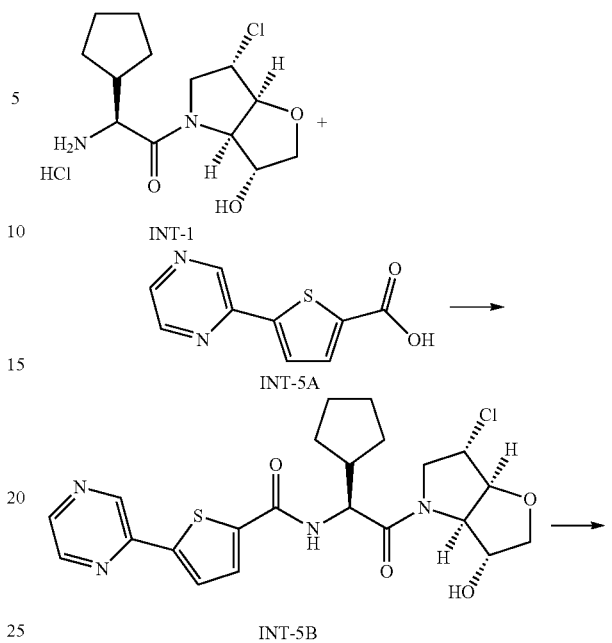

(i) 5-Boronothiophene-2-carboxylic acid (4.50 g, 26.2 mmol), 2-chloropyrazine (2.72 g, 23.8 mmol, 2.13 mL) and Na$_2$CO$_3$ (7.56 g, 71.4 mmol) were combined in water (30 mL) and DME (120 mL) and degassed with Ar. Tetrakis(triphenylphosphine)palladium(0) (1.20 g, 1.04 mmol) was added and the mixture was stirred at reflux under Ar for 18 h. The reaction mixture was poured into H$_2$O (200 mL) and washed with EtOAc (100 mL). The aqueous phase was acidified with aqueous HCl (2M) until pH 4-5 and extracted with EtOAc (2×200 mL). The combined organic layer was dried over Na$_2$SO$_4$ and concentrated in vacuo. The crude product was dissolved in 1,4-dioxane (50 mL), hydrochloric acid (4M in dioxane) was added. A precipitate was formed and the suspension was stirred for 2 h. The suspension was filtered and dried in vacuo to obtain INT-5A (0.500 g, 2.06 mmol, 9%) as an off-white solid.

(ii) A suspension of INT-1 (0.300 g, 0.922 mmol), INT-5A (0.190 g, 0.922 mmol), EDCI (0.212 g, 1.11 mmol), NEt$_3$ (0.449 mL, 3.23 mmol) and HOAt (0.013 g, 0.092 mmol) in DMF (4 mL) was stirred at RT for 144 h. The mixture was diluted with aqueous saturated NaHCO$_3$ (10 mL) and extracted with EtOAc (3×10 mL). The combined organic layer was washed with brine (10 mL), dried over Na$_2$SO$_4$ and concentrated in vacuo. Flash chromatography (MeCN (with 1% HCOOH)/H$_2$O 1:0 to 0:1, silica C-18) and lyophilisation gave INT-5B (0.065 g, 0.14 mmol, 15%). LCMS: calculated for [M+H]$^+$=477.14, found 477.1.

(iii) DMP (0.116 g, 0.273 mmol) was added to a solution of INT-5B (0.065 g, 0.14 mmol) in DCM (4 mL). The mixture was stirred at RT for 72 h. An aqueous solution of Na$_2$S$_2$O$_3$ (10%, 4 mL) was added and the mixture was stirred vigorously for 30 min. An aqueous saturated solution of NaHCO$_3$ (10 mL) was added and the layers were separated. The aqueous layer was extracted with DCM (10 mL). The combined organic layer was dried over Na$_2$SO$_4$. The filtrate was concentrated in vacuo. Purified by basic preparative HPLC (C18, MeCN (1% 10 mM NH$_4$HCO$_3$), 10 mM NH$_4$HCO$_3$ in H$_2$O) and lyophilized to obtain 5 (0.045 g, 0.095 mmol, 37%). LCMS: calculated for [M+H]$^+$=475.12, found 475.1. $^1$H NMR (400 MHz, DMSO-d$_6$) as a mixture of hydrates and rotamers δ 9.37-9.23 (m, 1H), 9.15-8.95 (m, 1H), 8.72-8.54 (m, 2H), 8.22-7.89 (m, 2H), 6.76 (s, 0.28H), 6.48 (s, 0.19H), 6.39 (s, 0.28H), 5.77 (s, 0.19H), 5.20-3.43 (m, 8H), 2.47-2.24 (m, 1H), 1.88-1.00 (m, 8H) ppm.

Example 6

N—((S)-2-((3aS,6S,6aS)-6-chloro-3-oxotetrahydro-2H-furo[3,2-b]pyrrol-4(5H)-yl)-1-cyclopentyl-2-oxoethyl)-5-(5-fluoropyridin-3-yl)thiophene-2-carboxamide

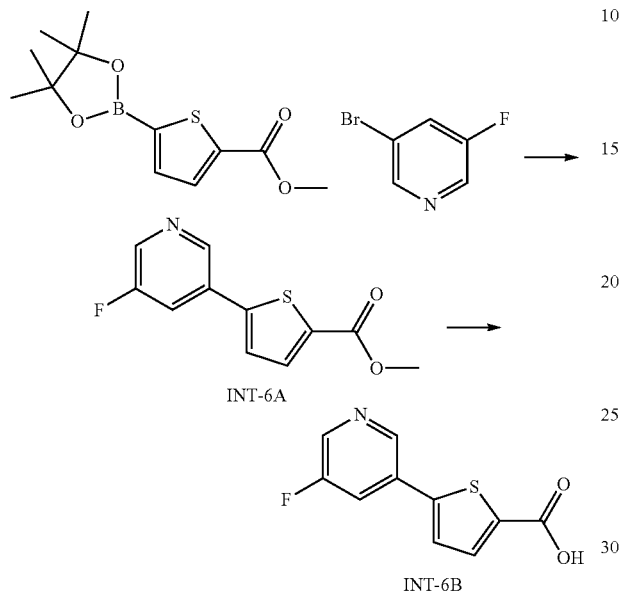

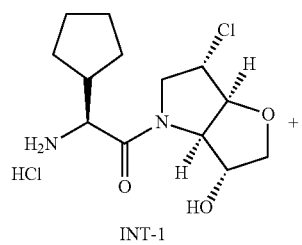

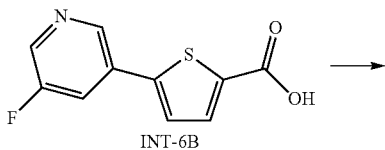

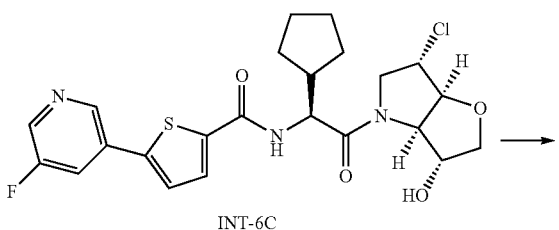

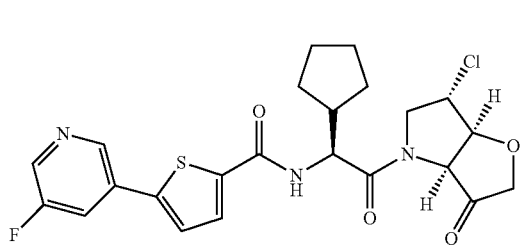

(i) A suspension of methyl 5-(4,4,5,5-tetramethyl-1,3,2-dioxaborolan-2-yl)thiophene-2-carboxylate (0.500 g, 1.87 mmol), Cs$_2$CO$_3$ (1.66 g, 5.09 mmol) and 5-bromo-3-fluoropyridine (0.298 g, 1.70 mmol) was degassed with Ar and [1,1-bis(diphenylphosphino)ferrocene]dichloropalladium (II) (0.077 g, 0.085 mmol) and stirred for 16 h at 100° C. An aqueous saturated solution of NaHCO$_3$ (20 mL) was added and the mixture was extracted with EtOAc (3×30 mL). The combined organic layer was washed with brine (10 mL), dried over Na$_2$SO$_4$ and concentrated in vacuo. Flash chromatography (EtOAc/heptane 0:1 to 1:0) afforded INT-6A (0.331 g, 1.33 mmol, 78%) as a white solid. LCMS: calculated for [M+H]$^+$=238.03, found 238.2.

(ii) At RT, LiOH.H$_2$O (0.179 g, 4.19 mmol) was added to a mixture of INT-6A (0.331 g, 1.33 mmol) in THF (20 mL) and water (8 mL). The reaction was stirred at RT for 16 h. The reaction was acidified with aqueous 1M HCl pH 2-3 (10 mL). The mixture was extracted with EtOAc (3×20 mL). The collected organic layer was washed with brine (20 mL), dried over Na$_2$SO$_4$ and concentrated in vacuo to give INT-6B (0.263 g, 1.12 mmol, 80%) as a white solid. LCMS: calculated for [M+H]$^+$=224.01, found 224.2.

(iii) A suspension of INT-1 (0.322 g, 0.990 mmol), INT-6B (0.221 g, 0.990 mmol), EDCI (0.228 g, 1.19 mmol), NEt$_3$ (0.401 g, 3.96 mmol, 0.552 mL) and HOAt (0.027 g, 0.20 mmol) in DMF (8 mL) was stirred at RT for 16 h. The mixture was diluted with EtOAc (20 mL) and washed with aqueous saturated solution of NaHCO$_3$ (20 mL) and brine (10 mL). The combined organic layer was dried over Na$_2$SO$_4$ and concentrated in vacuo. Flash chromatography (EtOAc/heptane 0:1 to 1:0) afforded INT-6C (0.500 g, 0.962 mmol, 97%). LCMS: calculated for [M+H]$^+$=494.12, found 494.2.

(iv) DMP (0.859 g, 2.02 mmol) was added to a solution of INT-6C (0.500 g, 0.962 mmol) in DCM (8 mL). The mixture was stirred at RT for 16 h. An aqueous solution of Na$_2$S$_2$O$_3$ (10%, 25 mL) was added and the mixture was stirred vigorously for 30 min. An aqueous saturated solution of NaHCO$_3$ (10 mL) was added and the layers were separated. The aqueous layer was extracted with DCM (2×10 mL). The combined organic layer was dried over Na$_2$SO$_4$ and concentrated in vacuo. The crude was dissolved in a small amount of boiling EtOAc and cooled to RT. Heptane was added until a precipitate formed and the mixture was reheated at boiling temperature until a clear solution was formed. The solution was left for 16 h standing at RT and the solids formed were filtered off. Lyophilisation (MeCN/H$_2$O) afforded 6 (0.267 g, 0.516 mmol, 51%). LCMS: calculated for [M+H]$^+$=492.11, found 492.2. $^1$H NMR (400 MHz, DMSO-d$_6$) as a mixture of hydrates and rotamers δ 9.18-8.92 (m, 1H), 8.91-8.76 (m, 1H), 8.65-8.52 (m, 1H), 8.39-8.10 (m, 1.4H), 8.08-7.97 (m, 0.6H), 7.83-7.71 (m, 1H), 6.74 (s, 0.38H), 6.48 (s, 0.28H), 6.36 (s, 0.38H), 5.77 (s, 0.28H), 5.29-3.40 (m, 8H), 2.47-2.30 (m, 1H), 1.88-1.04 (m, 8H) ppm.

Example 7

N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridazin-3-yl)thiazole-2-carboxamide

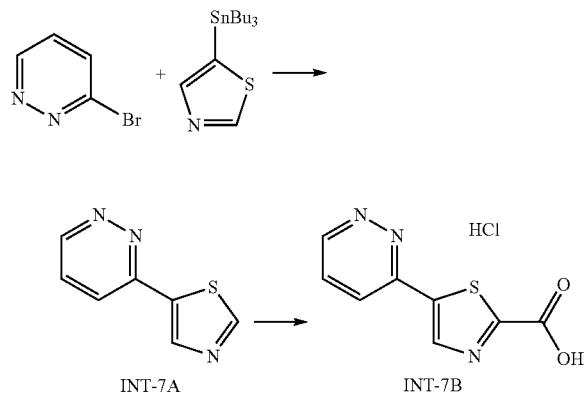

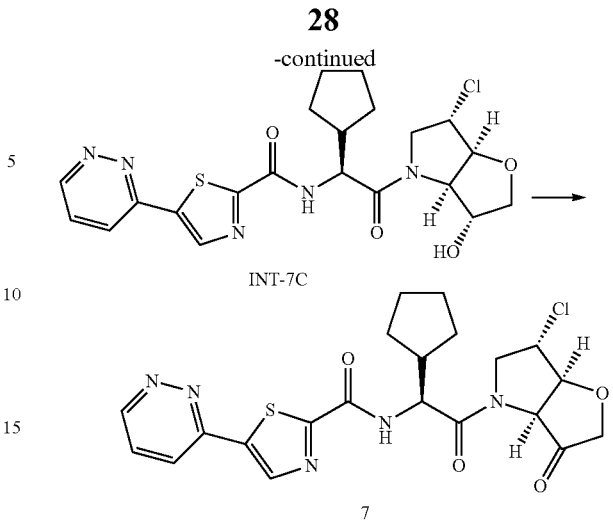

(i) 3-Bromopyridazine (1.02 g, 6.41 mmol), 5-(tributylstannyl)thiazole (2.00 g, 5.35 mmol), tri(furan-2-yl)phosphine (0.250 g, 1.07 mmol) and bis(dibenzylideneacetone) palladium (0.49 g, 0.53 mmol) were dissolved in dry dioxane (5 mL) and the resulting solution was heated at 90° C. and stirred for 16 h. The reaction was cooled to RT and filtered using a phase separator and the solvent was evaporated. Flash chromatography (EtOAc) afforded INT-7A (0.550 g, 3.37 mmol, 63%). LCMS: calculated for [M+H]$^+$=164.02, found 164.0.

(ii) Thiazole INT-7A (0.550 g, 3.37 mmol) was added to a solution of Lithium diisopropylamine (1M in THF/heptane/ethylbenzene, 26 mmol, 26 mL) in dry THF (10 mL) at −78° C. and the mixture was stirred for 30 min. CO$_2$ (solid) (14.8 g, 336 mmol) was added and the reaction was stirred for 2 h. The reaction was allowed to reach RT and the solvent was evaporated in vacuo. The crude was dissolved in water (10 mL) and washed with EtOAc (10 mL). The aqueous layer was acidified using a 1N HCl pH 4-5 solution and INT-7B (0.35 g) precipitated out as a yellow solid and was collected. LCMS: calculated for [M+H]$^+$=208.01, found 208.0.

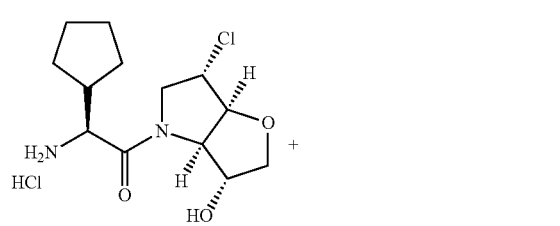

(iii) NEt$_3$ (0.788 g, 7.80 mmol, 1.09 mL) and propylphosphonic anhydride (50% w/w in DMF, 0.694 g, 1.09 mmol, 0.649 mL) were added consecutively to a solution of INT-1 (0.254 g, 0.780 mmol) and INT-7B (0.190 g, 0.780 mmol) in dry DMF (10 mL). The reaction was stirred at RT for 16 h. The reaction was diluted with EtOAc (30 mL) and washed with aqueous saturated NaHCO$_3$ (30 mL). The water layer was extracted with EtOAc (2×20 mL). The combined organic layer was washed with brine (20 mL), dried over Na$_2$SO$_4$ and concentrated in vacuo. The crude product was purified by flash column chromatography (MeOH/DCM 5:95) to afford INT-7C (0.200 g, 0.418 mmol, 54%). LCMS: calculated for [M+H]$^+$=478.12, found 478.2.

(iv) DMP (0.555 g, 1.31 mmol) was added to a solution of INT-7C (0.200 g, 0.418 mmol) in DCM (20 mL). The mixture was stirred at RT for 16 h. An aqueous solution of Na$_2$S$_2$O$_3$ (10%, 20 mL) was added and the mixture was stirred vigorously for 30 min. An aqueous saturated solution of NaHCO$_3$ (20 mL) was added and extracted with DCM (3×10 mL). The combined organic layer was dried over Na$_2$SO$_4$ and concentrated in vacuo. The crude product was purified by basic preparative HPLC (C18, MeCN (1% 10 mM NH$_4$HCO$_3$), 10 mM NH$_4$HCO$_3$ in H$_2$O) and lyophilization (MeCN/H$_2$O) afforded 7 (0.100 g, 0.210 mmol, 50%). LCMS: calculated for [M+H]$^+$=476.11, found 476.2. $^1$H-NMR (400 MHz, DMSO-d$_6$) as a mixture of hydrates and rotamers δ 9.35-9.24 (m, 1H), 8.97-8.80 (m, 1.46H), 8.59-8.32 (m, 1.40H), 8.18-8.10 (m, 0.14H), 7.99-7.87 (m, 1H), 6.74 (s, 0.37H), 6.57 (s, 0.37H), 6.53 (s, 0.15H), 5.85 (s, 0.15H), 5.42-3.46 (m, 8H), 2.54-2.30 (m, 1H), 1.92-1.17 (m, 8H) ppm.

Example 8

N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridin-4-yl)thiophene-2-carboxamide

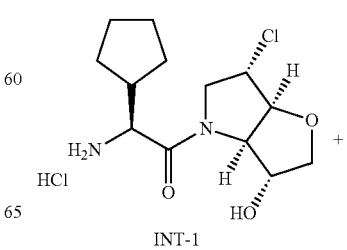

-continued

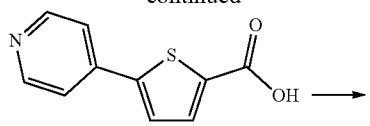

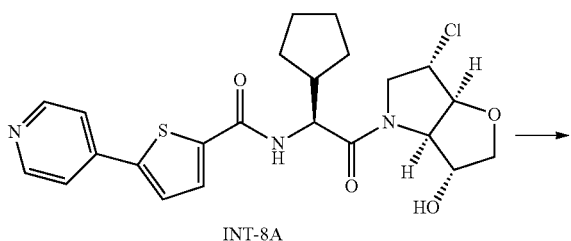

INT-8A

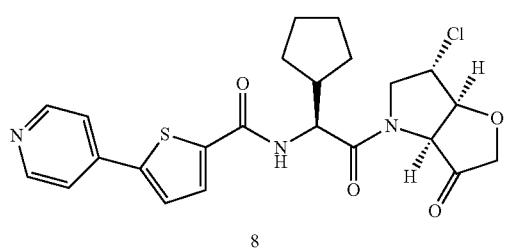

8

(i) A suspension of INT-1 (0.300 g, 0.922 mmol), 5-(pyridin-4-yl)thiophene-2-carboxylic acid (0.189 g, 0.922 mmol), EDCI (0.212 g, 1.11 mmol), NEt₃ (0.449 mL, 3.23 mmol) and HOAt (0.013 g, 0.092 mmol) in DMF (4 mL) was stirred at RT until completion. The RM was diluted with aqueous saturated NaHCO₃ (10 mL) and extracted with EtOAc (3×10 mL). The combined organic layer was washed with brine (10 mL), dried over Na₂SO₄ and concentrated in vacuo. Flash chromatography (EtOAc/heptane 0:1 to 1:0) afforded INT-8A (0.340 g, 0.714 mmol, 77%). LCMS: calculated for [M+H]⁺=476.14, found 476.1.

(ii) DMP (0.606 g, 1.429 mmol) was added to a solution of INT-8A (0.340 g, 0.714 mmol) in DCM (10 mL). The mixture was stirred at RT overnight. An aqueous solution of Na₂S₂O₃ (10%, 10 mL) was added and the RM was stirred vigorously for 30 min. An aqueous saturated solution of NaHCO₃ (50 mL) was added and the layers were separated. The aqueous layer was extracted with DCM (30 mL). The combined organic layer was dried over Na₂SO₄. The filtrate was concentrated in vacuo. Purified by basic preparative HPLC (C18, MeCN (1% 10 mM NH₄HCO₃), 10 mM NH₄HCO₃ in H₂O) and lyophilized to obtain 8 (0.092 g, 0.196 mmol, 28%). LCMS: calculated for [M+H]⁺=474.14, found 474.2. ¹H NMR (400 MHz, DMSO-d₆) as a mixture of hydrates and rotamers δ 9.17-8.93 (m, 1H), 8.70-8.55 (m, 2H), 8.41-7.98 (m, 1H), 7.91-7.78 (m, 1H), 7.78-7.39 (m, 2H), 6.73 (s, 0.29H), 6.48 (s, 0.21H), 6.36 (s, 0.29H), 5.77 (s, 0.21H), 5.18-3.43 (m, 8H), 2.48-2.26 (m, 1H), 1.86-1.03 (m, 8H) ppm.

Comparative Example C1

N—((S)-2-((3aS,6S,6aS)-6-chloro-3-oxotetrahydro-2H-furo[3,2-b]pyrrol-4(5H)-yl)-1-cyclopentyl-2-oxoethyl)-3-(pyridin-3-yl)benzamide

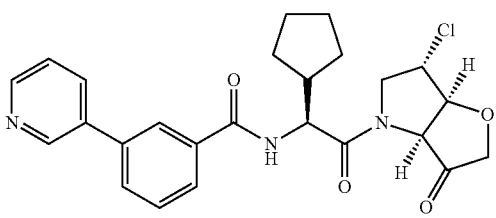

corresponds to example 17 of WO 2009/112839.

2. Biological Characterization—Cat S/K/L/B Functional Enzyme Assays

Reference and test compounds were assayed for inhibitory potency (IC50) against human cathepsins using the following assay setups:

Recombinant human cathepsins (CatS, CatK, CatL, CatB) were purchased from a Enzo Life Sciences. All assays were carried out in 96-well format using a buffer of 50 mM KH₂PO₄, 50 mM NaCl, 2 mM EDTA, 0.5 mM DTT and 1% Triton-X-100, pH 6.5 for Cathepsin S and a buffer of 50 mM NaOAc, 10 mM EDTA, 1 mM DTT and 0.01% Triton-X-100, pH 5.5 for CatK/L/B. For CatS, the enzyme (0.0007 mU/well) was incubated with fluorogeninc substrate (Z-VVR-AMC, 5 µM) at RT for 10 min. For CatK the enzyme (0.00175 mU/well) was incubated with fluorogeninc substrate (Z-FR-AMC, 40 µM) at RT for 10 min. For CatL, the enzyme (0.000874 mU/well) was incubated with fluorogeninc substrate (Z-VVR-AMC, 40 µM) at RT for 10 min. For CatB the enzyme was incubated with fluorogenic substrate (Z-VVR-AMC, 200 µM) at RT for 10 min. Flourogenic substrate turnover was detected using a microplate reader (Synergyl™ H4, BioTek). Ki values were calculated using the Cheng Prusoff equation (Cheng & Prusoff 1973).

| Compound | hCatS, Ki [µM] | hCatK, Ki [µM] | Selectivity Ki(hCatS)/Ki(hCatK) | hCatL, inhibition [%] at 31.6 µM |
|---|---|---|---|---|
| Example 1 | 0.1509 | 0.0015 | 99 | 72 |
| Example 2 | 0.3082 | 0.0007 | 453 | 45 |
| Example 3 | 0.1105 | 0.0021 | 53 | 73 |
| Example 4 | 0.0398 | 0.0018 | 22 | 73 |
| Example 5 | 0.3546 | 0.0021 | 169 | 81 |
| Example 6 | 0.1736 | 0.0031 | 55 | 42 |
| Example 7 | 0.2630 | 0.0053 | 50 | 62 |
| Example 8 | 0.1600 | 0.0008 | 210 | 50 |
| Comparative Example C1 (ex. 17 of WO2009/112839) | 0.0824 | 0.0148 | 6 | 0.925 (Ki) |

The invention claimed is:

1. A compound of the general formula (I)

(I)

wherein
R¹ represents H or F;
X represents S or O;
Y¹ and Y² independently represents CH or N;
Z¹, Z², Z³, Z⁴ and Z⁵ independently represents CH or N, with the proviso that 1, 2 or 3 of Z¹, Z², Z³, Z⁴ and Z⁵ represent N;
m denotes 0, 1 or 2;
n denotes 0, 1, 2 or 3;
each R² and each R³ is independently selected from the group consisting of F; Cl; Br; CN; CF₃; CF₂H; CFH₂; CF₂Cl; CFCl₂; C₁₋₄-alkyl; C(=O)—(C₁₋₄-alkyl); C(=O)—NH₂; C(=O)—N(H)(C₁₋₄-alkyl); C(=O)—N(C₁₋₄-alkyl)₂; OH; O—C₁₋₄-alkyl; OCF₃; OCF₂H; OCFH₂; OCF₂Cl; OCFCl₂; NH₂; N(H)(C₁₋₄-alkyl); N(C₁₋₄-alkyl)₂; N(H)—C(=O)—(C₁₋₄-alkyl); N(C₁₋₄-alkyl)-C(=O)—(C₁₋₄-alkyl); N(H)—S(=O)₂—(C₁₋₄-alkyl); N(H)—C(=O)—NH₂; N(H)—C(=O)—N(H)(C₁₋₄-alkyl); N(H)—C(=O)—N(C₁₋₄-alkyl)(C₁₋₄-alkyl); S—(C₁₋₄-alkyl); S(=O)—(C₁₋₄-alkyl); S(=O)₂—(C₁₋₄-alkyl); S(=O)₂—N(H)(C₁₋₄-alkyl); cyclopropyl; O-cyclopropyl; NH-cyclopropyl; N(H)—C(=O)-cyclopropyl; S(=O)-(cyclopropyl) and S(=O)₂-(cyclopropyl);
wherein the above-mentioned substituents C₁₋₄-alkyl and cyclopropyl may in each case be unsubstituted or substituted one or more times by identical or different substituents; and the above-mentioned substituent C₁₋₄-alkyl may in each case be branched or unbranched;
in the form of an individual stereoisomer or a mixture thereof; in the form of a tautomer; of a free compound; of an N-oxide; or in the form of a solvate and/or of a physiologically acceptable salt.

2. A compound according to claim 1, wherein R¹ is H.

3. A compound according to claim 1, wherein
Y¹ represents CH or N and Y² represents CH; or
Y¹ represents CH and Y² represents CH or N.

4. A compound according to claim 1, wherein
X represents S.

5. A compound according to claim 1, wherein
X represents S, Y¹ represents CH and Y² represents CH.

6. A compound according to claim 1, wherein
X represents S, Y¹ represents CH and Y² represents N.

7. A compound according to claim 1, wherein the compound of the general formula (I) is a compound according to general formula (Ia):

(Ia)

wherein Z represents m denotes 0 or 1;
Y² represents N or CH;
R² is selected from the group consisting of F; Cl; Br; CN; CF₃; CF₂H; CFH₂; CF₂Cl; CFCl₂; C₁₋₄-alkyl; C(=O)—(C₁₋₄-alkyl); C(=O)—NH₂; C(=O)—N(H)(C₁₋₄-alkyl); C(=O)—N(C₁₋₄-alkyl)₂; OH; O—C₁₋₄-alkyl; OCF₃; OCF₂H; OCFH₂; OCF₂Cl; OCFCl₂; NH₂; N(H)(C₁₋₄-alkyl); N(C₁₋₄-alkyl)₂; N(H)—C(=O)—(C₁₋₄-alkyl); N(C₁₋₄-alkyl)-C(=O)—(C₁₋₄-alkyl); N(H)—S(=O)₂—(C₁₋₄-alkyl); N(H)—C(=O)—NH₂; N(H)—C(=O)—N(H)(C₁₋₄-alkyl); N(H)—C(=O)—N(C₁₋₄-alkyl)(C₁₋₄-alkyl); S—(C₁₋₄-alkyl); S(=O)—(C₁₋₄-alkyl); S(=O)₂—(C₁₋₄-alkyl); S(=O)₂—N(H)(C₁₋₄-alkyl); cyclopropyl; O-cyclopropyl; NH-cyclopropyl; N(H)—C(=O)-cyclopropyl; S(=O)-(cyclopropyl) and S(=O)₂-(cyclopropyl);
n denotes 0, 1 or 2 and
R³ is independently selected from the group consisting of F; Cl; Br; CN; CF₃; CF₂H; CFH₂; CF₂Cl; CFCl₂; C₁₋₄-alkyl; C(=O)—(C₁₋₄-alkyl); C(=O)—NH₂; C(=O)—N(H)(C₁₋₄-alkyl); C(=O)—N(C₁₋₄-alkyl)₂; OH; O—C₁₋₄-alkyl; OCF₃; OCF₂H; OCFH₂; OCF₂Cl; OCFCl₂; NH₂; N(H)(C₁₋₄-alkyl); N(C₁₋₄-alkyl)₂; N(H)—C(=O)—(C₁₋₄-alkyl); N(C₁₋₄-alkyl)-C(=O)—(C₁₋₄-alkyl); N(H)—S(=O)₂—(C₁₋₄-alkyl); N(H)—C(=O)—NH₂; N(H)—C(=O)—N(H)(C₁₋₄-alkyl); N(H)—C(=O)—N(C₁₋₄-alkyl)(C₁₋₄-alkyl); S—(C₁₋₄-alkyl); S(=O)—(C₁₋₄-alkyl); S(=O)₂—(C₁₋₄-alkyl); S(=O)₂—N(H)(C₁₋₄-alkyl); cyclopropyl; O-cyclopropyl; NH-cyclopropyl; N(H)—C(=O)-cyclopropyl; S(=O)-(cyclopropyl) and S(=O)₂-(cyclopropyl).

8. A compound according to claim 7, wherein
m denotes 0;
n denotes 0, 1 or 2 and
R³ is independently selected from the group consisting of F; Cl; CN; CF₃; CF₂H; CFH₂CH₃; CH₂CH₃; CH(CH₃)₂; C(=O)CH₃; C(=O)NH₂; C(=O)N(H)(CH₃); C(=O)N(CH₃)₂; OH; OCH₃; OCF₃; OCF₂H; OCFH₂; NH₂; N(H)(CH₃); N(CH₃)₂; N(H)—C(=O)CH₃; N(H)—S(=O)₂CH₃; S(=O)CH₃; S(=O)₂CH₃; S(=O)₂—N(H)(CH₃); cyclopropyl and O-cyclopropyl.

9. A compound according to claim 7, wherein Z represents

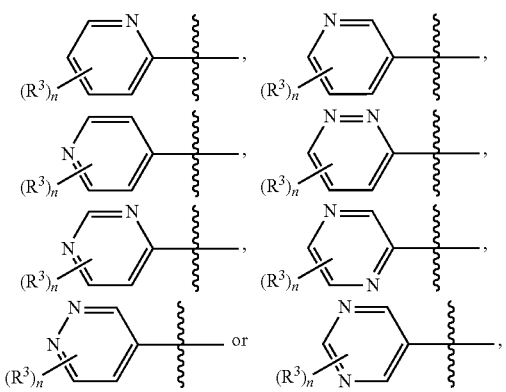

m denotes 0;
n denotes 0 or 1; and
R³ is independently selected from the group consisting of F; Cl; CN; CF₃; CF₂H; CFH₂CH₃; CH₂CH₃; CH(CH₃)₂; C(=O)CH₃; C(=O)NH₂; C(=O)N(H)(CH₃); C(=O)N(CH₃)₂; OH; OCH₃; OCF₃; OCF₂H; OCFH₂; NH₂; N(H)(CH₃); N(CH₃)₂; N(H)—C(=O)CH₃; N(H)—S(=O)₂CH₃; S(=O)CH₃; S(=O)₂CH₃; S(=O)₂—N(H)(CH₃); cyclopropyl and O-cyclopropyl.

10. A compound according to claim 1, wherein the compound of the general formula (I) is a compound according to general formula (Ib):

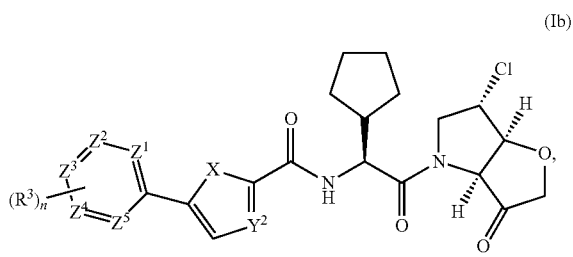

wherein Y² represents CH or N;
Z³, Z⁴ and Z⁵ each represent CH and Z¹ represents N; or
Z¹, Z⁴ and Z⁵ each represent CH and Z³ represents N; or
Z¹, Z³ and Z⁵ each represent CH and Z⁴ represents N; or
Z¹, Z³ and Z⁴ each represent CH and Z⁵ represents N;
n denotes 0 or 1; and
R³ is selected from the group consisting of F; Cl; CN; CF₃; CF₂H; CFH₂; CH₃; OCH₃ and OCF₃.

11. A compound according to claim 10, wherein
Y² represents CH; n denotes 0 and Z³, Z⁴ and Z⁵ each represent CH and and Z¹ represents N; or
Z¹, Z⁴ and Z⁵ each represent CH and Z³ represents N.

12. A compound according to claim 1, which is selected from the group consisting of:

1   N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridazin-3-yl)thiophene-2-carboxamide
2   N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridin-3-yl)thiophene-2-carboxamide
3   N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyrimidin-5-yl)thiophene-2-carboxamide
4   N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridazin-4-yl)thiophene-2-carboxamide
5   N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyrazin-2-yl)thiophene-2-carboxamide
6   N—((S)-2-((3aS,6S,6aS)-6-chloro-3-oxotetrahydro-2H-furo[3,2-b]pyrrol-4(5H)-yl)-1-cyclopentyl-2-oxoethyl)-5-(5-fluoropyridin-3-yl)thiophene-2-carboxamide
7   N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridazin-3-yl)thiazole-2-carboxamide
8   N—((S)-2-((3aS,6S,6aS)-6-chloro-3-oxotetrahydro-2H-furo[3,2-b]pyrrol-4(5H)-yl)-1-cyclopentyl-2-oxoethyl)-5-(pyridine-4-yl)thiophene-2-carboxamide in the form of an individual stereoisomer or a mixture thereof; in the form of a tautomer; of a free compound; of an N-oxide; or in the form of a solvate and/or of a physiologically acceptable salt.

13. A pharmaceutical composition comprising at least one compound according to claim 1.

14. A method for the treatment of a disorder selected from the group consisting of nociceptive pain; neuropathic pain; erosive osteoarthritis (EO); erosive osteoarthritis of the hand; Sjögren's Syndrom; rheumatoid arthritis (RA); psoriatic arthrithis (PsA); Psoriasis; Spondylarthritis; ankylosing spondylitis; osteoporosis; Complex Regional Pain Syndrome; CRPS I; Lupus erythematodes (SLE); Lupus nephritis; multiple sclerosis (MS); diabetes; chronic obstructive pulmonary disease (COPD); COPD subpopulation with osteoporosis; asthma; and severe asthma subpopulation with osteoporosis; said method comprising administering to a patient in need thereof an effective amount therefor of at least one compound according to claim 1.

* * * * *